US010556716B2

(12) United States Patent
Ramos

(10) Patent No.: US 10,556,716 B2
(45) Date of Patent: Feb. 11, 2020

(54) COLLAPSIBLE MEDICAL CONTAINERS

(71) Applicant: Miguel David Ramos, Salt Lake City, UT (US)

(72) Inventor: Miguel David Ramos, Salt Lake City, UT (US)

(*) Notice: Subject to any disclaimer, the term of this patent is extended or adjusted under 35 U.S.C. 154(b) by 0 days.

(21) Appl. No.: 15/380,165

(22) Filed: Dec. 15, 2016

(65) Prior Publication Data

US 2017/0174386 A1   Jun. 22, 2017

Related U.S. Application Data

(60) Provisional application No. 62/269,907, filed on Dec. 18, 2015, provisional application No. 62/344,778, filed on Jun. 2, 2016.

(51) Int. Cl.

| B65D 5/36 | (2006.01) |
|---|---|
| B65D 5/60 | (2006.01) |
| B65D 5/02 | (2006.01) |
| A61B 50/30 | (2016.01) |
| B65D 5/66 | (2006.01) |
| A61B 50/36 | (2016.01) |
| A61B 50/20 | (2016.01) |
| B65D 5/50 | (2006.01) |

(Continued)

(52) U.S. Cl.
CPC ............ B65D 5/3607 (2013.01); A61B 50/20 (2016.02); A61B 50/30 (2016.02); A61B 50/36 (2016.02); A61B 50/362 (2016.02); B65D 5/02 (2013.01); B65D 5/0281 (2013.01); B65D 5/3614 (2013.01); B65D 5/3621 (2013.01); B65D 5/3692 (2013.01); B65D 5/5007 (2013.01); B65D 5/60 (2013.01); B65D 5/6697 (2013.01); A61B 2017/00526 (2013.01); A61B 2050/005 (2016.02); A61B 2050/0081 (2016.02)

(58) Field of Classification Search
CPC .......... B65D 5/02; B65D 5/60; B65D 5/0281; B65D 5/36; B65D 5/3621; B65D 5/3692; B65D 5/6697; B31B 5/26; B31B 5/60; B31B 2201/26; B31B 2201/60; B31B 2203/003; B31B 2203/006; A61B 50/30
USPC .......................... 229/108.1, 117.01, 117, 183
See application file for complete search history.

(56) References Cited

U.S. PATENT DOCUMENTS

| 3,371,844 A | 3/1968 | Parrella |
|---|---|---|
| 4,182,477 A | 1/1980 | Paige |

(Continued)

FOREIGN PATENT DOCUMENTS

| GB | 2458149 | 9/2009 |
|---|---|---|
| JP | 3105431 | 10/2004 |
| KR | 2020140000487 | 1/2014 |

OTHER PUBLICATIONS

International Search Report and Written Opinion dated Mar. 24, 2017 for PCT/US2016/066894.
European Search Report dated May 9, 2019 for EP16876668.1.

*Primary Examiner* — Christopher R Demeree
(74) *Attorney, Agent, or Firm* — Stoel Rives LLP

(57) ABSTRACT

Containers that are capable of transitioning from a collapsed configuration to an uncollapsed configuration. The containers, when in a collapsed configuration, may have a relatively low profile. When in an uncollapsed configuration, the containers can function as receptacles for receiving solids or liquids. Some containers can be manufactured by folding a foldable sheet that includes a plurality of openings.

25 Claims, 20 Drawing Sheets

(51) Int. Cl.
*A61B 17/00* (2006.01)
*A61B 50/00* (2016.01)

(56) References Cited

U.S. PATENT DOCUMENTS

| | | | |
|---|---|---|---|
| 4,391,366 A | | 7/1983 | Hirata |
| 4,406,380 A | * | 9/1983 | Paige .................. B65D 5/3621 229/117 |
| 5,209,391 A | * | 5/1993 | Krautsack ............ B65D 5/0218 229/104 |
| 5,299,734 A | * | 4/1994 | Lane ........................ B65B 5/10 229/120.15 |
| 6,189,776 B1 | | 2/2001 | Smith et al. |
| 2008/0054060 A1 | | 3/2008 | Greenfield |
| 2013/0284753 A1 | | 10/2013 | Kellmann |
| 2014/0217161 A1 | | 8/2014 | Chalifoux |
| 2014/0251865 A1 | | 9/2014 | Merrill |
| 2014/0339292 A1 | | 11/2014 | Graham et al. |
| 2015/0203240 A1 | | 7/2015 | Mengistu et al. |
| 2015/0203288 A1 | | 7/2015 | Hunter |
| 2016/0176594 A1 | * | 6/2016 | Holley, Jr. ......... B65D 71/0022 206/141 |

* cited by examiner

COLLAPSIBLE MEDICAL CONTAINERS

CROSS-REFERENCE TO RELATED APPLICATIONS

This application claims the benefit of U.S. Provisional Patent Application No. 62/269,907, titled COLLAPSIBLE CONTAINER OF FOLDED PLANAR STRUCTURE AND IMPERMEABLE LINER, filed on Dec. 18, 2015. This application also claims the benefit of U.S. Provisional Patent Application No. 62/344,778, titled COLLAPSIBLE MEDICAL CONTAINERS, filed on Jun. 2, 2016, the entire contents of U.S. Provisional Patent Application No. 62/344,778 are hereby incorporated by this reference.

TECHNICAL FIELD

The present disclosure generally relates to containers, including containers that are capable of transitioning from a collapsed configuration to an uncollapsed configuration. Related articles and methods are also disclosed. The containers may be configured to hold or retain medical devices, medical waste, medical samples, or other materials.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1A:
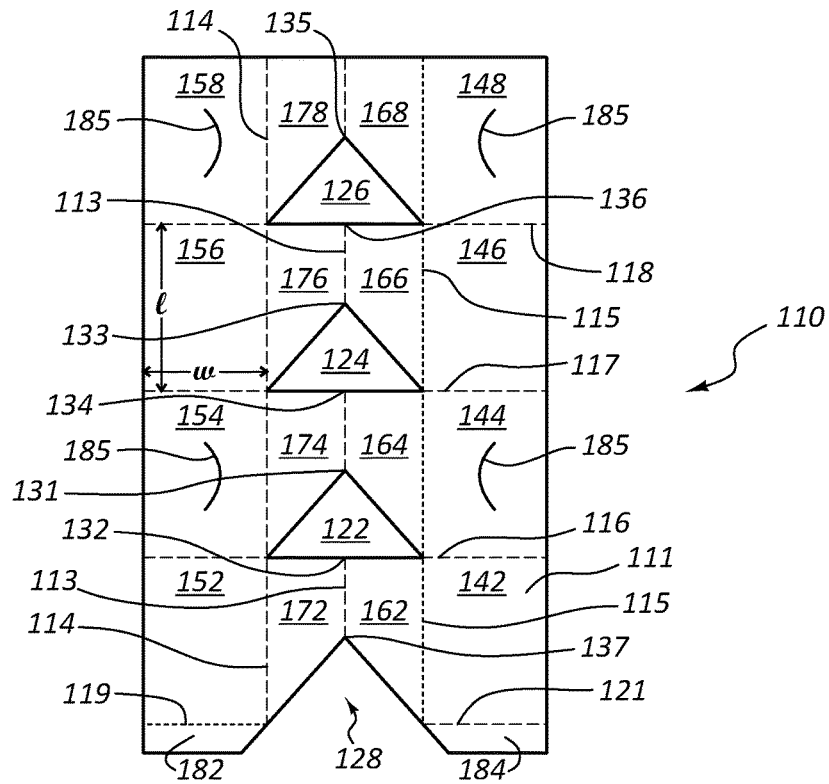
FIG. 1A is a view of a first side of a foldable sheet.

Collapsible containers may be used in a variety of situations and circumstances. For example, collapsible containers may be used in the medical field as a receptacle for liquids and/or solids.

In some embodiments, a collapsible container may serve as a receptacle for liquid or solid medical waste. For example, during a medical procedure, a practitioner may remove solid or liquid waste from a patient (e.g., via a syringe) and then discard the removed waste into a waste receptacle. In some embodiments, an absorbent material is disposed within the waste receptacle to soak up the liquid waste. In some embodiments, the container includes a lid and/or a slit valve that minimizes splatter that can occur when waste is delivered (e.g., ejected from a syringe) into the container.

In other embodiments or circumstances, a collapsible container may be used to soak a guidewire in a liquid (e.g., water, saline, antibacterial solution, and/or anticoagulant) prior to use of the guidewire in a medical procedure. Hydration of the guidewire, such as by storage in a liquid, may increase the lubricity of the guidewire as it is advanced within a patient, protect the guidewire from contaminants, and/or reduce coagulation around the guidewire once it is inserted into the patient. Other uses for collapsible containers, such as for carrying food or as a container in case of emergency, are also within the scope of this disclosure.

Some non-collapsible containers may suffer from one or more drawbacks relative to collapsible containers. For example, collapsible containers may be disposed in a collapsed configuration that has a relatively low profile that allows for compact storage and efficient shipping. Additionally or alternatively, collapsible containers may be made from relatively inexpensive, lightweight, and/or biodegradable materials that facilitate disposal of the container after use.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling between two or more entities. Two components may be coupled to each other even though they are not in direct contact with each other. The phrase "attached to" refers to interaction between two or more entities which are in direct contact with each other and/or are separated from each other only by a fastener of any suitable variety (e.g., an adhesive).

As used herein, the term "isosceles triangle" refers to a triangle with at least two sides of equal length. When used with reference to a collapsible container or a component thereof, the terms "interior," "exterior," "upward," and "downward" are to be understood with reference to the collapsible container when in an upright, uncollapsed configuration. The terms "interior wall" and "exterior wall" refer to different walls, and not to opposite sides of a single panel. A "foldable" sheet is a sheet that is capable of being bent such that the foldable sheet, when unconstrained after having been bent, retains a crease. A "collapsible" container is a folded container that is capable of transitioning from a first folded configuration in which the container is configured for use (i.e., the uncollapsed configuration) to a second folded configuration in which the container adopts a low-profile configuration (i.e., the collapsed configuration). The term "collapsible container" does not encompass embodiments in which the container transitions from a use configuration to a low-profile configuration by simply unfolding the container to form a single-layer sheet.

Figure 1B:
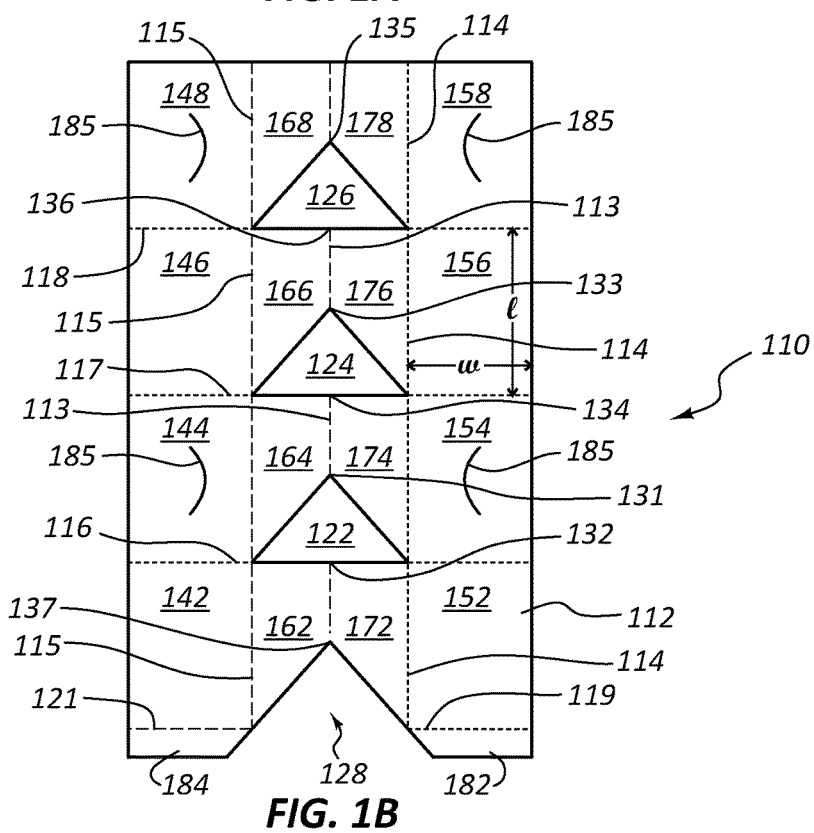
FIG. 1B is a view of a second side of the foldable sheet of FIG. 1A.

FIGS. 1A and 1B provide views of a first side 111 (FIG. 1A) and a second side 112 (FIG. 1B) of a foldable sheet 110 that is configured to be manipulated into a collapsible container. Stated differently, a method for manufacturing a collapsible container may include the step of obtaining a foldable sheet, such as the foldable sheet 110 depicted in FIGS. 1A and 1B.

As shown in FIGS. 1A and 1B, the foldable sheet 110 may be elongate in shape and include a plurality of folds 113, 114, 115, 116, 117, 118, 119, 121, a plurality of openings 122, 124, 126, a notch 128, and one or more tabs 182, 184.

In the depicted embodiment, the plurality of folds includes a first longitudinal fold 113, a second longitudinal fold 114, and a third longitudinal fold 115. The folds 113, 114, 115 may be substantially parallel to one another. For example, the first longitudinal fold 113 may be disposed between and substantially parallel to both the second longitudinal fold 114 and the third longitudinal fold 115. In some embodiments, the first longitudinal fold 113 is disposed along the longitudinal axis of the sheet 110.

The plurality of folds of the sheet 110 may also include a first transverse fold 116, a second transverse fold 117, and a third transverse fold 118. The transverse folds 116, 117, 118 may be disposed substantially perpendicular to the longitudinal folds 113, 114, 115 when the sheet is disposed flat as a single layer. The sheet 110 may also include a first tab fold 119 and a second tab fold 121.

FIGS. 1A and 1B indicate the directions of the folds 113, 114, 115, 116, 117, 118, 119, 121 using different types of dashed lines. For instance, in FIGS. 1A and 1B, a fold denoted by a dashed line of relatively long dashes (e.g., line 114 of FIG. 1A) indicates that the planar panels on either side of the fold tend to come out of the page relative to the fold (as the sheet is folded), while a fold denoted by a dashed line of relatively short dashes (e.g., line 115 of FIG. 1A) indicates that the planar panels on either side of the fold tend to go into the page relative to the fold (as the sheet is folded). In some embodiments, the folds 113, 114, 115, 116, 117, 118, 119, 121 are introduced into the sheet 110 prior to folding the sheet 110 into a collapsible container as described below. Stated differently, the sheet 110 may be folded along the line corresponding to each fold 113, 114, 115, 116, 117, 118, 119, 121 prior to further folding the sheet 110 into a collapsible container.

As noted above, the sheet 110, when unfolded as shown in FIGS. 1A and 1B to form a single layer, may define a plurality of openings 122, 124, 126. For example, in some embodiments, the sheet 110 may include a first number of openings 122, 124, 126 that is one less than the number of lateral sides of a collapsible container that is made from the sheet 110. Each opening of the plurality of openings 122, 124, 126 may include a tapered end 131, 133, 135 and a non-tapered end 132, 134, 136 disposed opposite the tapered end 131, 133, 135. The non-tapered end 132, 134, 136 of each opening 122, 124, 126 may lie along one of the transverse folds 116, 117, 118. As shown in the depicted embodiment, each opening 122, 124, 126 may be oriented such that the tapered ends 131, 133, 135 of all the openings 122, 124, 126 point in the same direction when the foldable sheet 110 is unfolded to form a single layer.

In some embodiments, one or more openings 122, 124, 126 may be substantially triangular in shape. For example, the openings 122, 124, 126 may be shaped as an isosceles triangle. In some embodiments, each opening 122, 124, 126 lies along (e.g., is centered about) a longitudinal axis of the sheet 110 when the sheet 100 is disposed flat as a single layer.

As noted above, the foldable sheet 110 may further include a notch 128. For example, in the depicted embodiment, the notch 128 lies along a longitudinal axis of the foldable sheet 110. The notch 128 may be similar or substantially identical in shape to the openings 122, 124, 126, except that the notch 128 is not surrounded on all sides by portions of the foldable sheet 110. As shown in FIGS. 1A and 1B, the notch 128 may include a tapered end 137 that points in the same direction as the tapered ends 131, 133, 135 of the openings 122, 124, 126. In some embodiments, the sum of the number of openings 122, 124, 126 and the number of notches 128 may equal the number of lateral sides of a collapsible container that is made from the sheet 110.

The folds 113, 114, 115, 116, 117, 118, 119, 121, the openings 122, 124, 126, and the notch 128 of the sheet 110 may define a plurality of planar panels of the sheet 110. For example, in some embodiments, the folds 113, 114, 115, 116, 117, 118, 119, 121 of the sheet 110 define a first interior wall segment 142, a second interior wall segment 144, a third interior wall segment 146, a fourth interior wall segment 148, a first exterior wall segment 152, a second exterior wall segment 154, a third exterior wall segment 156, and a fourth exterior wall segment 158. The folds 113, 114, 115, 116, 117, 118, 119, 121, the openings 122, 124, 126, and the notch 128 may also define a first interior base segment 162, a second interior base segment 164, a third interior base segment 166, a fourth interior base segment 168, a first exterior base segment 172, a second exterior base segment 174, a third exterior base segment 176, and a fourth exterior base segment 178.

The interior wall segments 142, 144, 146, 148 and the exterior wall segments 152, 154, 156, 158 may each be substantially rectangular in shape. Further, in some embodiments, each of the rectangularly shaped wall segments is substantially the same size as each of the other rectangularly shaped wall segments.

In some embodiments, one or more wall segments 142, 144, 146, 148, 152, 154, 156, 158 has a length (l) and a width (w). The length (l) may define the length of one or more dimensions (e.g., the length and width) of a collapsible container formed from the sheet 110 when the collapsible container is in an uncollapsed configuration. The width (w) may define a length of a different dimension (e.g., the height) of a collapsible container formed from the sheet 110 when the collapsible container is in an uncollapsed configuration. One of ordinary skill in the art, with the benefit of this disclosure, will recognize that the length (l) and width (w) of the wall segments 142, 144, 146, 148, 152, 154, 156, 158 may be varied to obtain containers of different sizes.

In the depicted embodiment, the base segments 162, 164, 166, 168, 172, 174, 176, 178 are trapezoidal in shape. However, this shape is not meant to be limiting, as base segments of other shapes are also within the scope of this disclosure.

The sheet 110 may also include one or more tabs, such as a first tab 182 and a second tab 184. The tabs 182, 184 may be designed to facilitate coupling of planar wall segments to one another. For example, the first tab 182 may be configured to couple one planar wall segment (e.g., the first exterior wall segment 152) of an exterior wall to another planar wall segment (e.g., fourth exterior wall segment 158) of the exterior wall. The second tab 184 may be configured to couple one planar wall segment (e.g., the first interior wall segment 142) of an interior wall to another planar wall segment (e.g., the fourth interior wall segment 148) of the interior wall.

In some embodiments, the sheet 100 includes one or more slits 185. In the depicted embodiment, the slits 185 are generally U-shaped incisions in the sheet 110. However, one of ordinary skill in the art, with the benefit of this disclosure will recognize that slits of different shapes are within the scope of this disclosure. Some embodiments do not include slits.

The sheet 110 may be made from any foldable material. For example, in some embodiments, the sheet 110 comprises cellulose. More particularly, the sheet 110 may include or be made from paper, cardboard, or some other cellulose-based product. In other or further embodiments, the sheet 110 includes and/or is made from plastic or metal (e.g., metal foil).

Figure 2:
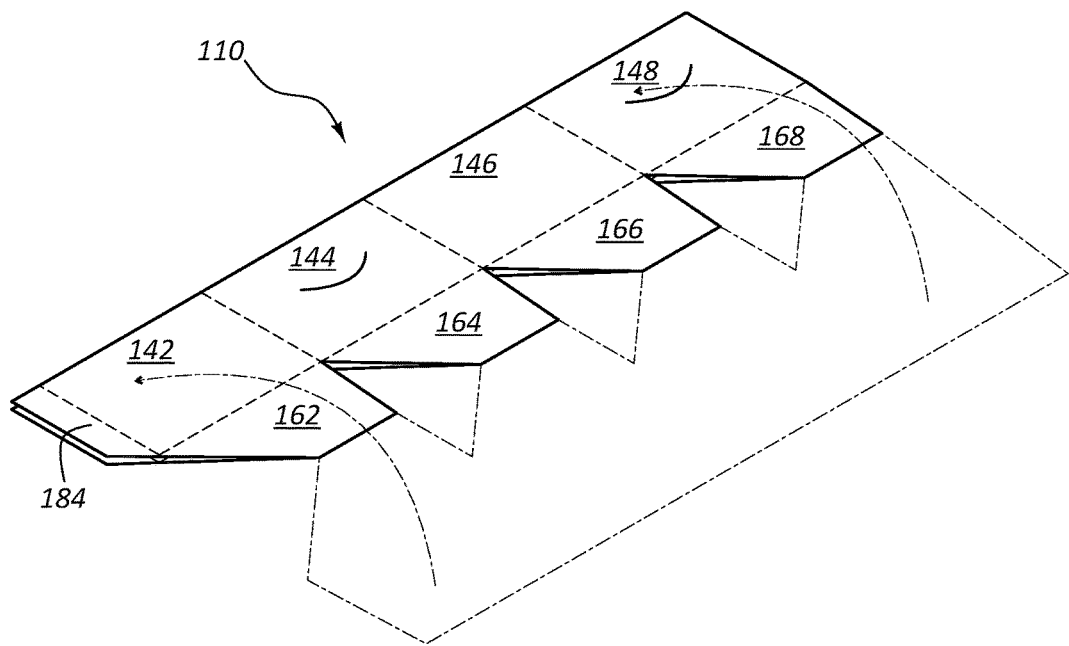
FIGS. 2, 3, 4, 5, and 6 are perspective views of the foldable sheet of FIGS. 1A-1B in differently folded states.

The sheet 110 of FIGS. 1A and 1B may be manipulated as described below in connection with FIGS. 2-8 to form a collapsible container. For example, a portion of the sheet 110 as shown in FIG. 1A may be folded as shown in FIG. 2. The view provided in FIG. 2 shows the interior wall segments 142, 144, 146, and 148, the interior base segments 162, 164, 166, 168, and the second tab 184.

Figure 3:
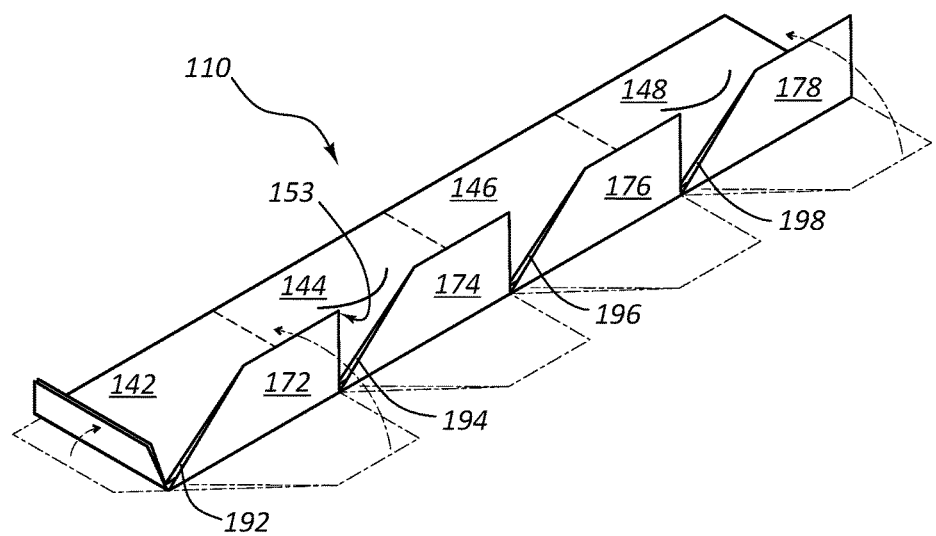

Once the sheet 110 is folded as shown in FIG. 2, the base segments 162, 164, 166, 168 may then be at least partially bent toward the interior wall segments 142, 144, 146, 148. For example, as shown in FIG. 3, the base segments 162, 164, 166, 168 may be bent toward the interior wall segments 142, 144, 146, 148 such that the base segments 162, 164, 166, 168 are disposed substantially perpendicular to the interior wall segments 142, 144, 146, 148. The bending of the base segments 162, 164, 166, 168 toward the interior wall segments 142, 144, 146, 148 reveals both a plurality of slots 192, 194, 196, 198 and a plurality of exterior base segments 172, 174, 176, 178.

Figure 4:
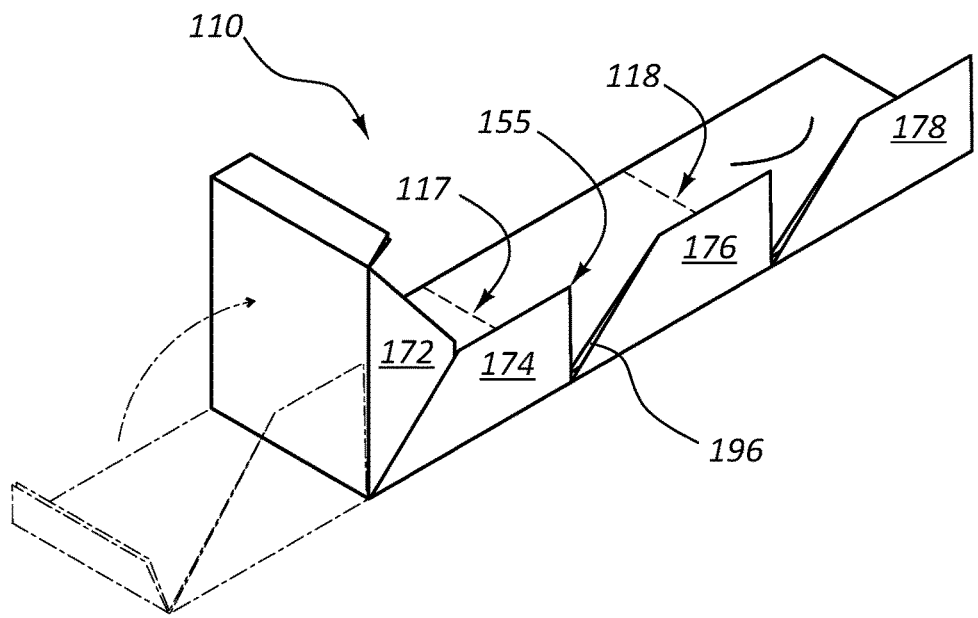
Figure 5:
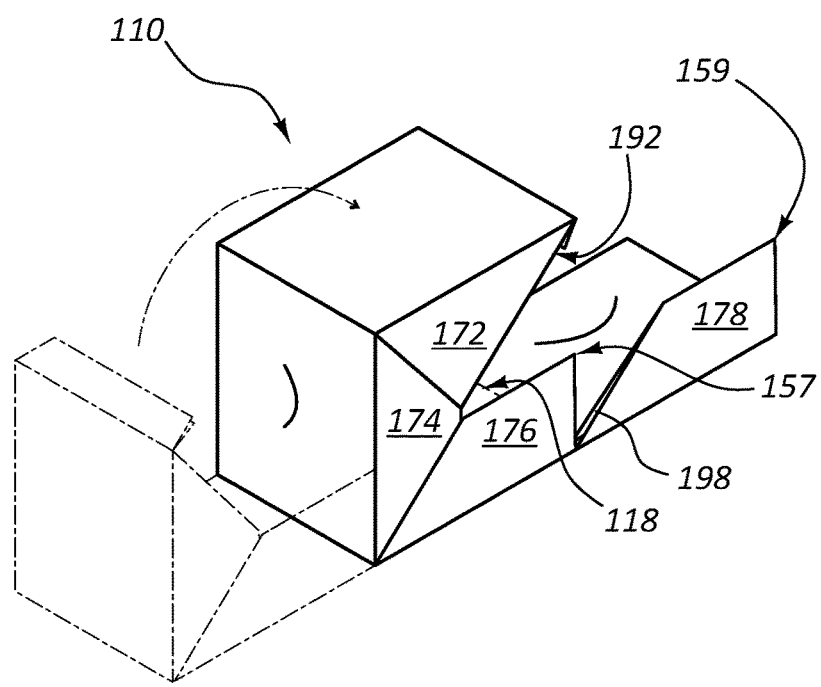

A first corner 153 at the junction of the first interior base segment 162 and the first exterior base segment 172 may then be inserted into the second slot 194 such that the sheet 110 is disposed as shown in FIG. 4. A second corner 155 at the junction of the second interior base segment 164 and the second exterior base segment 174 may then be inserted into the third slot 196 such that the sheet 110 is disposed as shown in FIG. 5. Stated differently, the portion of the sheet 110 that is disposed on the left side of the fold 117 may be rotated about the fold 117 to insert the second corner 155 into the third slot 196.

Figure 6:
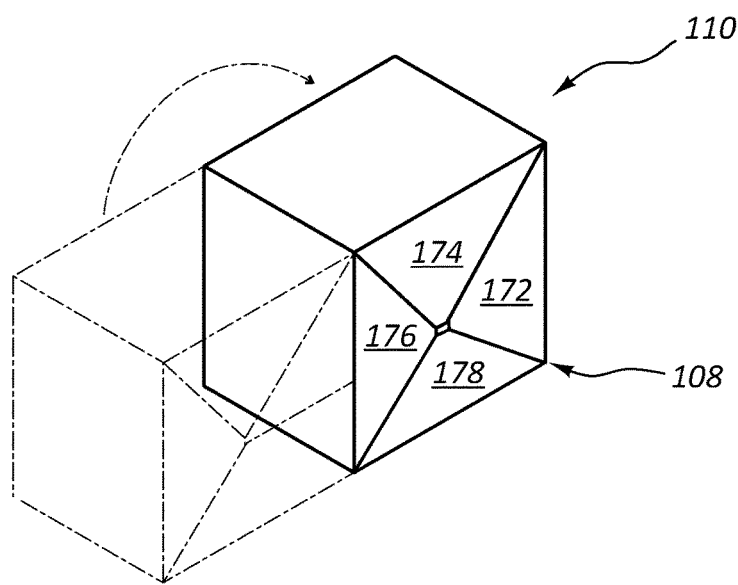

A third corner 157 at the junction of the third interior base segment 166 and the third exterior base segment 176 may then be inserted into the fourth slot 198, and the fourth corner 159 may be inserted into the first slot 192 to form the folded sheet 110 shown in FIG. 6. Stated differently, the portion of the sheet 110 that is disposed on the left of the fold 118 may be rotated relative to the remainder of the sheet 110 to form the folded sheet 110 depicted in FIG. 6. In some embodiments, the third corner 157 may be inserted into the fourth slot 198 at the same time that the fourth corner 159 is inserted into the first slot 192. The resulting box-shaped structure has a substantially planar base 108 that includes the first exterior base segment 172, the second exterior base segment 174, the third exterior base segment 176, the fourth exterior base segment 178, and the interior base segments (not shown in FIG. 6).

Figure 7:
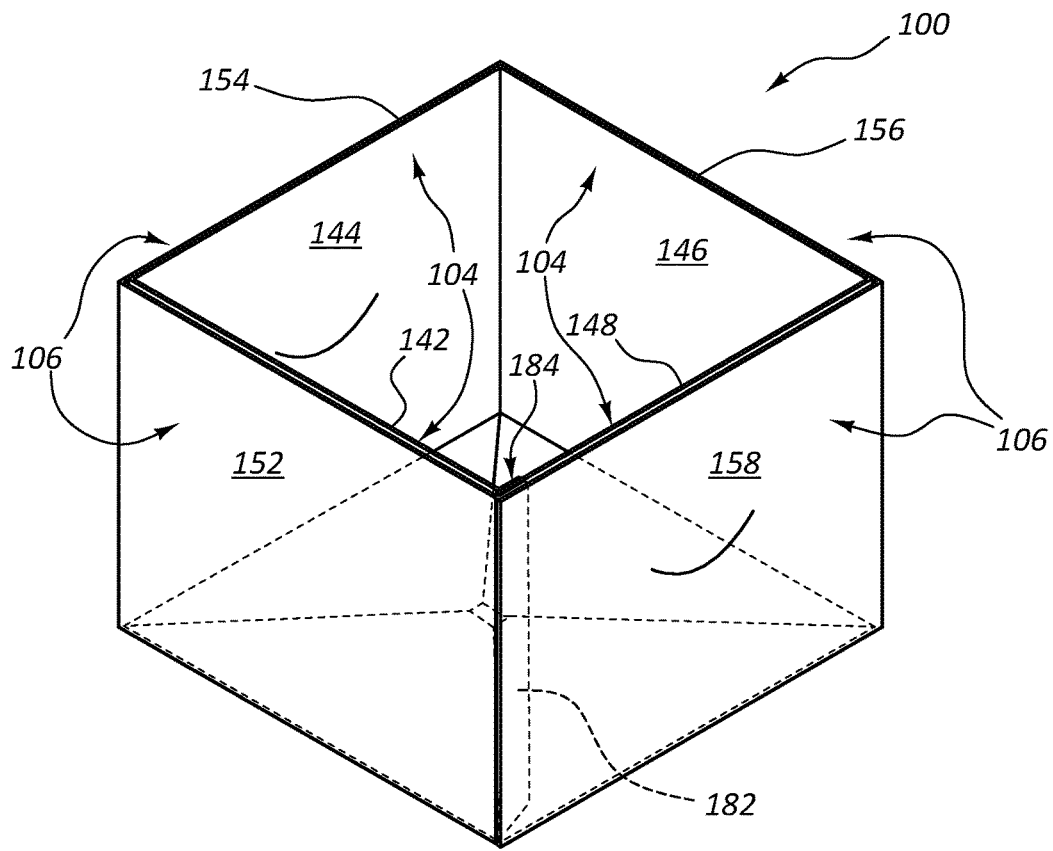
FIG. 7 is a perspective view of a collapsible container formed from the sheet of FIGS. 1A-7, with the collapsible container in an uncollapsed configuration.
Figure 8:
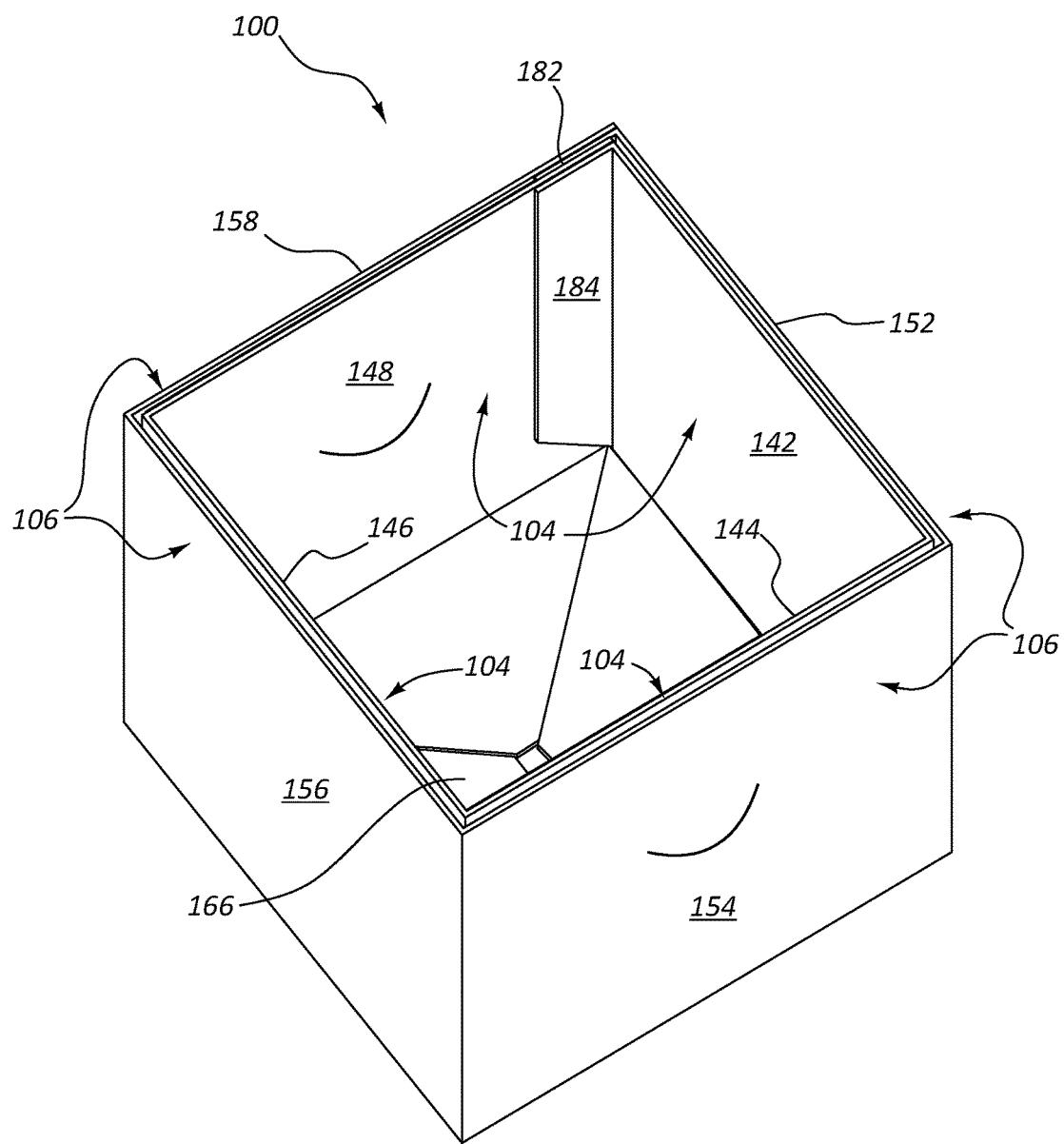
FIG. 8 is another perspective view of the collapsible container of FIG. 7 in an uncollapsed configuration.

A first tab 182 and/or a second tab 184 may then be secured to other elements of the sheet 110 to form a collapsible container 100 as shown in FIGS. 7 and 8. For example, the first tab 182 may be secured to the fourth exterior wall segment 158 to form a continuous exterior side wall 106 that includes the first exterior wall segment 152, the second exterior wall segment 154, the third exterior wall segment 156, and the fourth exterior wall segment 158. The first tab 182 may be secured to the fourth exterior wall segment 158 in any suitable manner. For example, in some embodiments, the first tab 182 is attached to the fourth exterior wall segment 158 via an adhesive, although other methods of securing the first tab 182 to the exterior wall are within the scope of this disclosure. Further, although the first tab 182 as shown in FIGS. 7 and 8 is attached to an inner face of the fourth exterior wall segment 158, in other embodiments, the tab 182 may be secured to an outer face of the fourth exterior wall segment 158.

In some embodiments, the second tab 184 may be secured (e.g., via an adhesive) to the fourth interior wall segment 148 to form a continuous interior wall 104 that includes the first interior wall segment 142, the second interior wall segment 144, the third interior wall segment 146, and the fourth interior wall segment 148. While the second tab 184 is attached to an inner face of the fourth interior wall segment 148 in the embodiment depicted in FIGS. 7 and 8, the second tab 184 may be secured to an outer face of the fourth interior wall segment 148 in other embodiments.

One of ordinary skill in the art, with the benefit of this disclosure, will understand that the processes described above for manufacturing the collapsible container 100 from the sheet 110 are exemplary, and do not limit the scope of this disclosure. Indeed, methods that differ somewhat from those described above may be employed to manufacture the collapsible container 100 and related embodiments. For example, in some embodiments, a foldable sheet may include additional features that would improve manufacturability, assembly, economy, useability, increase permissible tolerances, etc.

Figure 9:
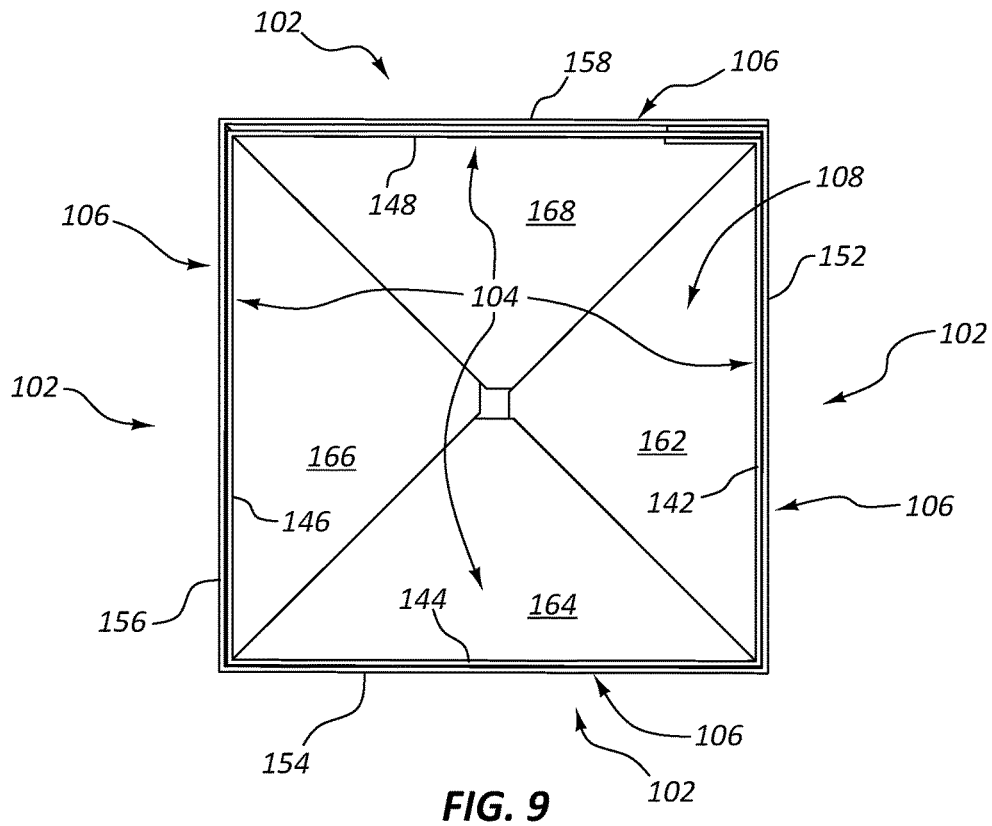
FIG. 9 is a top view of the collapsible container of FIGS. 7-8.
Figure 10:
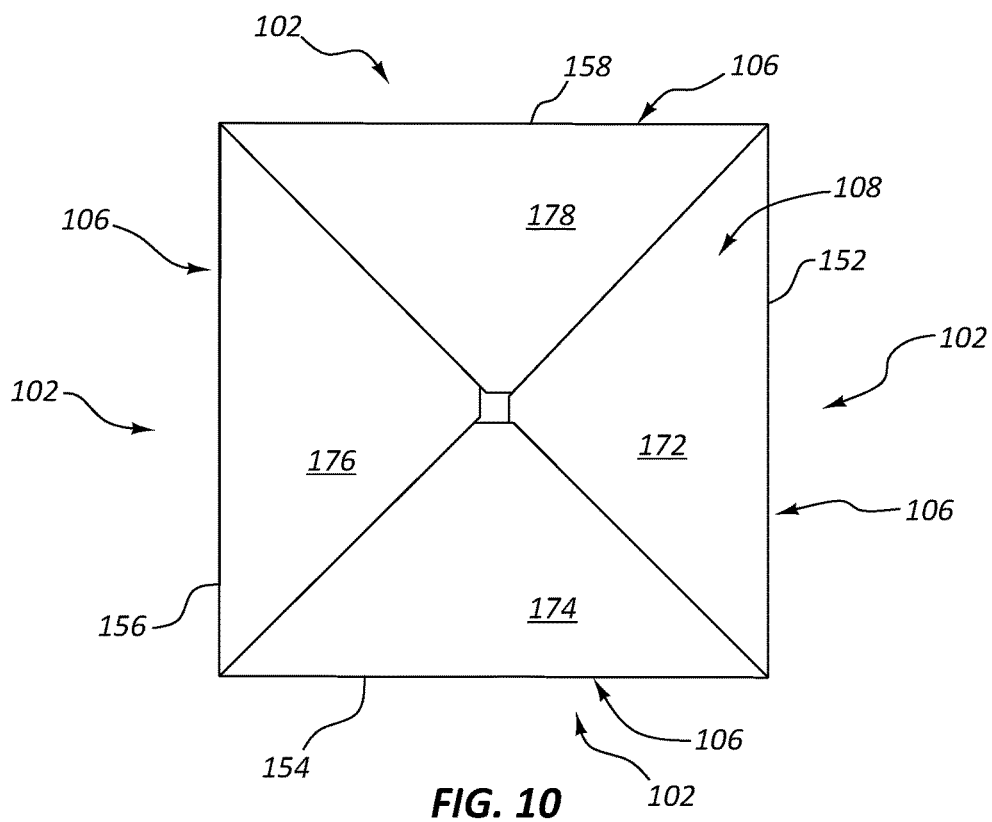
FIG. 10 is a bottom view of the collapsible container of FIGS. 7-9.

FIGS. 9 and 10 provide alternative views of the collapsible container 100 in an uncollapsed configuration. More specifically, FIG. 9 provides a top view of the collapsible container 100 in an uncollapsed configuration, while FIG. 10 provides a bottom view of the collapsible container 100 in an uncollapsed configuration. As shown in FIGS. 9 and 10, the collapsible container 100, when in the uncollapsed configuration, is a three-dimensional structure that comprises an open top end, a plurality of lateral sides 102, and a substantially closed base 108.

The collapsible container 100, when in the uncollapsed configuration, is a dual-walled container 100 that has four lateral sides 102. The collapsible container 100 may include an interior side wall 104 and an exterior side wall 106 that form the plurality of sides 102. The side walls 104, 106 are both portions of the sheet 110. Each of the interior side wall 104 and the exterior side wall 106 include a plurality of planar wall segments. For example, the interior side wall 104 may include the first interior wall segment 142, the second interior wall segment 144, the third interior wall segment 146, and the fourth interior wall segment 148. The exterior side wall 106 may include the first exterior wall segment 152, the second exterior wall segment 154, the third exterior wall segment 156, and the fourth exterior wall segment 158.

The interior side wall 104 and the exterior side wall 106 may each extend around the periphery of the collapsible container 100 to form a convex polygon. In some embodiments, each of the internal angles of the convex polygon are greater than or substantially equal to 30°. For example, the internal angles of the convex polygon may be greater than or substantially equal to 60°, 90°, 120°, or 135° degrees. In some embodiments, the convex polygon formed by the interior side wall 104 and the exterior side wall 106 is a regular polygon, such as a square, a regular hexagon, or a regular octagon. The dual-walled structure of the container 100 may increase the strength and/or rigidity of the container 100.

While the container 100 is depicted as having a square base, one of ordinary skill in the art with the benefit of this disclosure will appreciate that modifications may be made to the sheet 110 to form an irregularly shaped polygon, such as a rectangle. For example, to form a container with a rectangular base, the length (l) of the wall segments 142, 146, 152, 156 may be increased or decreased relative to the length of the wall segments 144, 148, 154, 158. In such rectangular embodiments, the length of the base segments 162, 166, 172, 176 may also be increased or decreased relative to the base segments 164, 168, 174, 178 by the same amount, while keeping the openings 122, 124, 126 and the notch 128 the same size.

When the collapsible container 100 is in the uncollapsed configuration, the container 100 has a base 108 that is formed from the interior base segments 162, 164, 166, 168 and the exterior base segments 172, 174, 176, 178.

Figure 11:
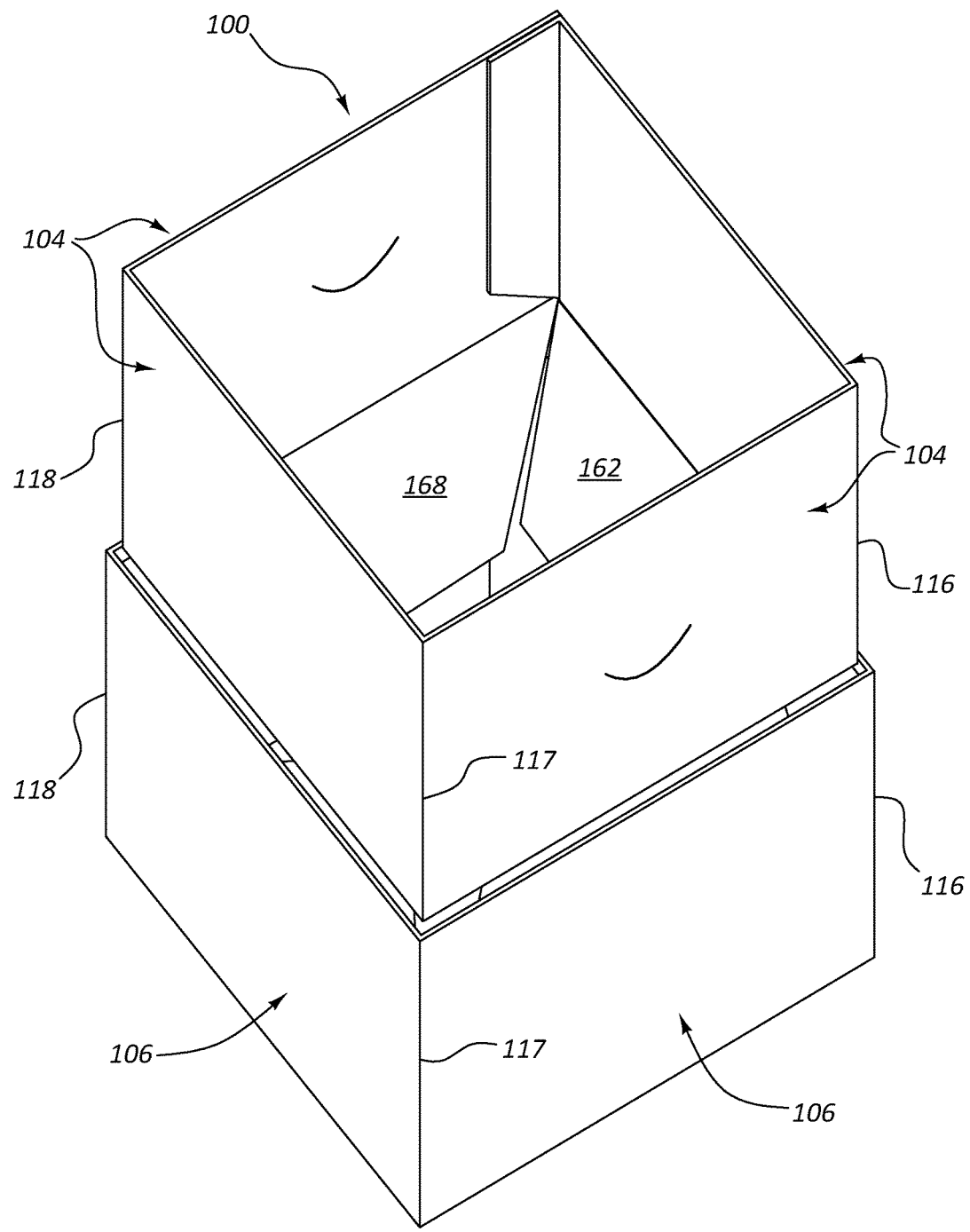
FIG. 11 is a perspective view of the collapsible container of FIGS. 7-10 in an extended configuration.
Figure 12:
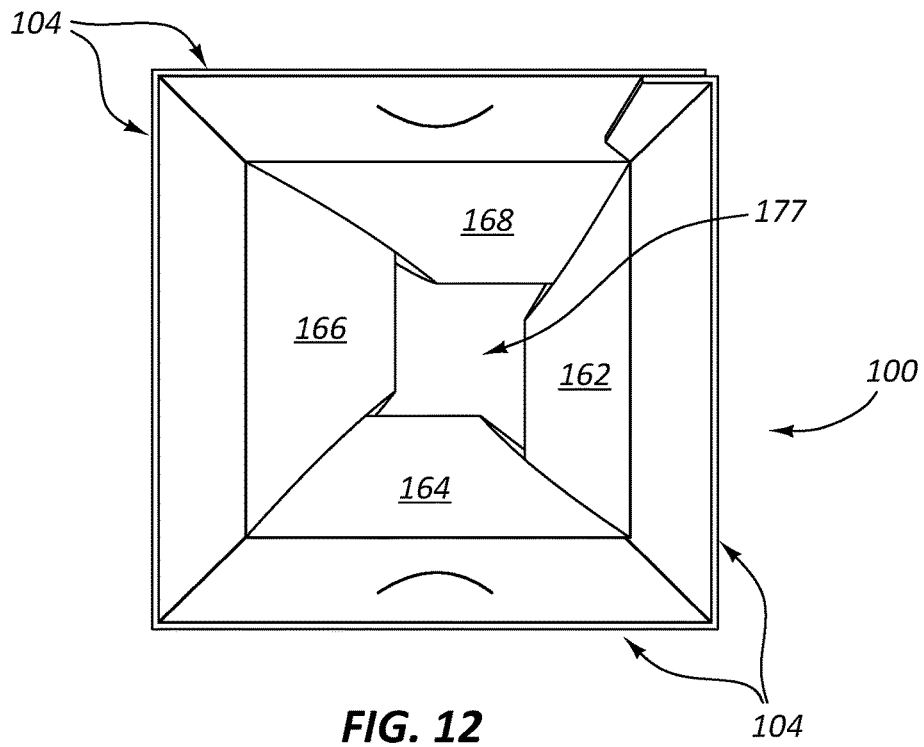
FIG. 12 is a top view of the collapsible container of FIGS. 7-11 in an extended configuration.
Figure 13:
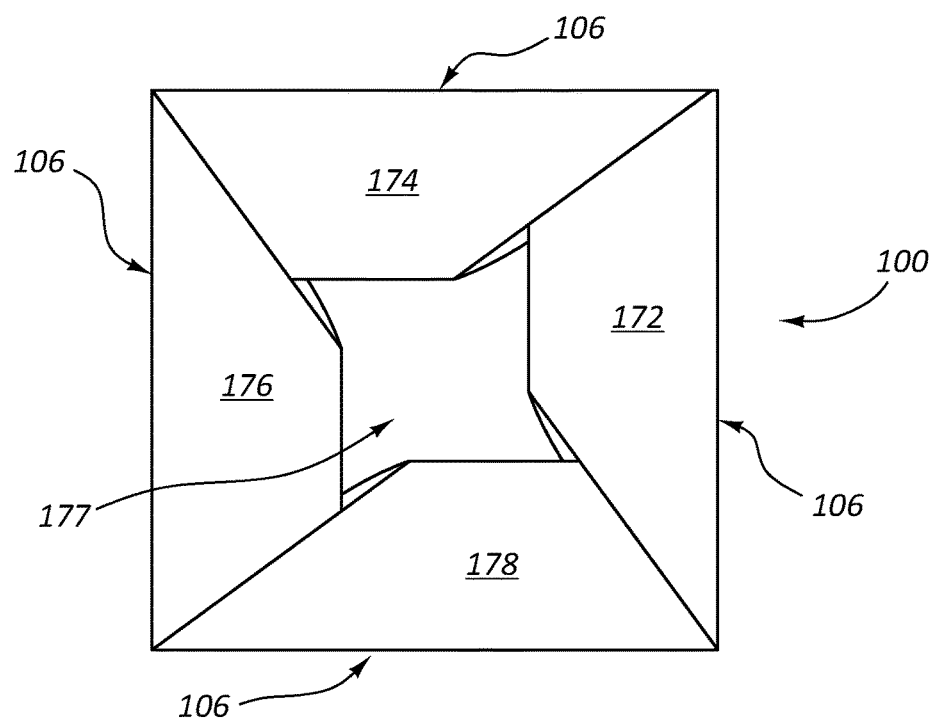
FIG. 13 is a bottom view of the collapsible container of FIGS. 7-12 in an extended configuration.
Figure 14:
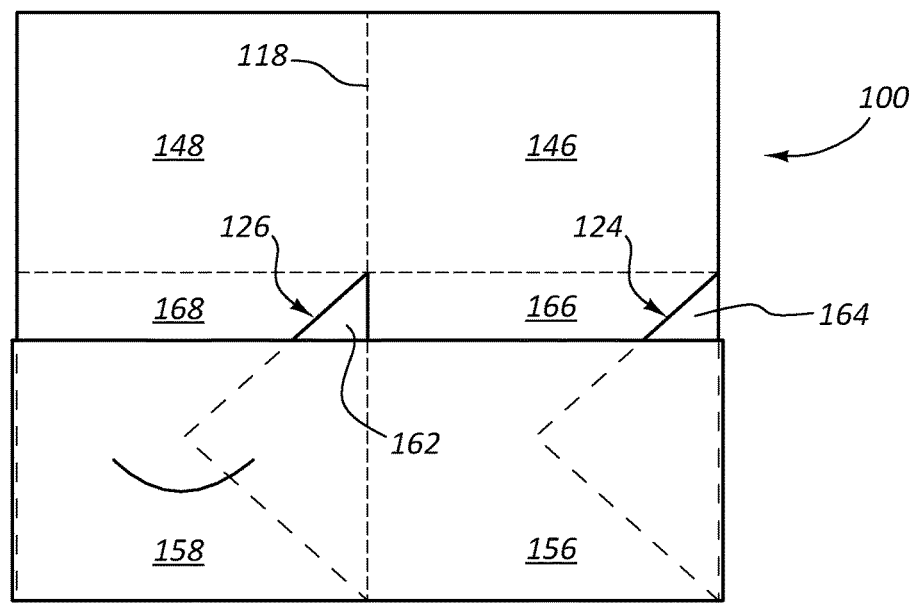
FIG. 14 is a side view of the collapsible container of FIGS. 7-13 in a collapsed configuration.

The collapsible container 100 is configured to transition from an uncollapsed configuration (e.g., as shown in FIGS. 7-10) to a collapsed configuration (e.g., as shown in FIG. 14) and vice versa. For example, to transition the collapsible container 100 from the uncollapsed configuration to the collapsed configuration, the interior side wall 104 may first be displaced (e.g., lifted) relative to the exterior side wall 106. For example, the interior side wall 104 may be lifted relative to the exterior side wall 106 such that the collapsible container 100 adopts the configuration shown in FIGS. 11-13, which may be referred to as an "extended" configuration. FIG. 11 provides a perspective view of the collapsible container 100 in the extended configuration, while FIGS. 12 and 13 provide top (FIG. 12) and bottom (FIG. 13) views of the collapsible container 100 in the same configuration. In the extended configuration, an entirety of the interior side wall 104 is disposed above the exterior side wall 106.

As the interior side wall 104 is lifted relative the exterior side wall 106, the base segments 162, 164, 166, 168, 172, 174, 176, 178 may transition from a position in which all of the base segments 162, 164, 166, 168, 172, 174, 176, 178 lie substantially in a single horizontal plane to form the base of the container 100 to a configuration in which the base segments 162, 164, 166, 168, 172, 174, 176, 178 do not lie in a single horizontal plane. More particularly, as the interior side wall 104 is lifted, the interior base segments 162, 164, 166, 168 may each rotate away from a corresponding exterior base segment 172, 174, 176, 178 such that each interior base segment 162, 164, 166, 168 is angled relative to the corresponding exterior base segment 172, 174, 176, 178. For example, the first interior base segment 162 may be angled relative to the first exterior base segment 172 when the collapsible container 100 is in the extended configuration. Such displacement of the interior base segments 162, 164, 166, 168 and the exterior base segments 172, 174, 176, 178 may expand and/or form an opening 177 that extends through the center of the container 100.

From the extended configuration shown in FIGS. 11-13, the container 100 may be collapsed such that an entirety of the container 100 lies in substantially a single plane as shown in FIG. 14 by displacing the edge of the container 100 defined by the fold 118 toward an edge of the container defined by the fold 116. The view provided in FIG. 14 shows the interior wall segments 146, 148, the exterior wall segments 156, 158, and the interior base segments 162, 164, 166, 168, and the openings 124, 126. When in the collapsed configuration, the collapsible container 100 may be in a relatively low-profile configuration that allows for compact storage and shipping.

Alternatively, instead of collapsing the container by displacing the fold 118 toward the fold 116, the container 100 may be collapsed by displacing the edge of the container defined by the fold 117 toward an edge of the container 100 that is located where the first interior wall segment 142 abuts the fourth interior wall segment 148 and the first exterior wall segment 152 abuts the fourth exterior wall segment 158. One of ordinary skill in the art, with the benefit of this disclosure, will recognize that transitioning the container 100 from the uncollapsed configuration to the collapsed configuration as described herein is not simply the inverse of the process for assembling the container 100.

The collapsible container may transition from the collapsed configuration to the uncollapsed configuration in substantially the reverse manner. For example, the collapsible container 100 may transition from a collapsed configuration in which the planar wall segments of the interior side wall 104 and the planar wall segments of the exterior side wall 106 lie substantially in a single plane to an uncollapsed configuration by (1) displacing the interior side wall 104 and the exterior side wall 106 such that the interior side wall 104 and the exterior side wall 106 each form a polygon of suitable shape and then (2) displacing the interior side wall 104 in a downward direction such that the interior side wall 104 is disposed directly inside of the exterior side wall 106.

Figure 15:
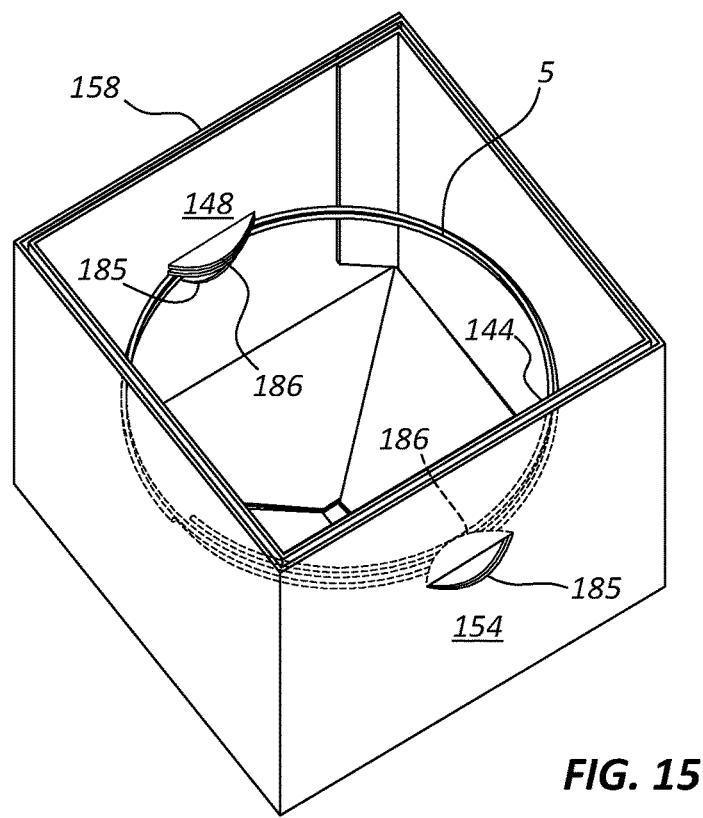
FIG. 15 is a perspective view of the collapsible container of FIGS. 7-14 in an uncollapsed configuration with arms extending inward from the sides of the container.

In some embodiments, such as the embodiment depicted in FIG. 15, the collapsible container 100 further includes one or more arms 186 that are formed from the slits 185 in the wall segments (e.g., planar wall segments 144, 148, 154, 158) of the collapsible container 100. In the depicted embodiment, the slits 185 may line up with one another when the collapsible container 100 is in an uncollapsed configuration. For example, the U-shaped slit 185 in the planar wall segment 144 and the U-shaped slit 185 in the planar wall segment 154 may line up with one another when the collapsible container 100 is in an uncollapsed configuration. Likewise, the U-shaped slit 185 in the fourth interior wall segment 148 may line up with the U-shaped slit 185 in the fourth exterior wall segment 158. A portion of the wall segments may then be pushed inward to form an arm 186. The arm 186 may serve as a ledge that can be used to retain a medical appliance, such as a guidewire 5.

In other embodiments, one or more portions of the wall segments may be pushed in an outward direction, thereby preventing displacement of the interior wall 104 relative to the exterior wall 106. In other words, the arm 186, when bent outward, may function as a lock that prevents transitioning of the collapsible container 100 from the uncollapsed configuration to the collapsed configuration.

In some embodiments, the collapsible container 100 may include a liner (not shown). The liner may sit predominantly inside the collapsible container. In some embodiments, the liner is a liquid-impermeable liner. In some embodiments, the liner is semipermeable. The liner may protect the remaining portions of the collapsible container from contact with a liquid or solid substance that is placed in the container 100. The liner can be made from one or more of plastic, cloth, metal, and foil, among other materials.

Figure 16:
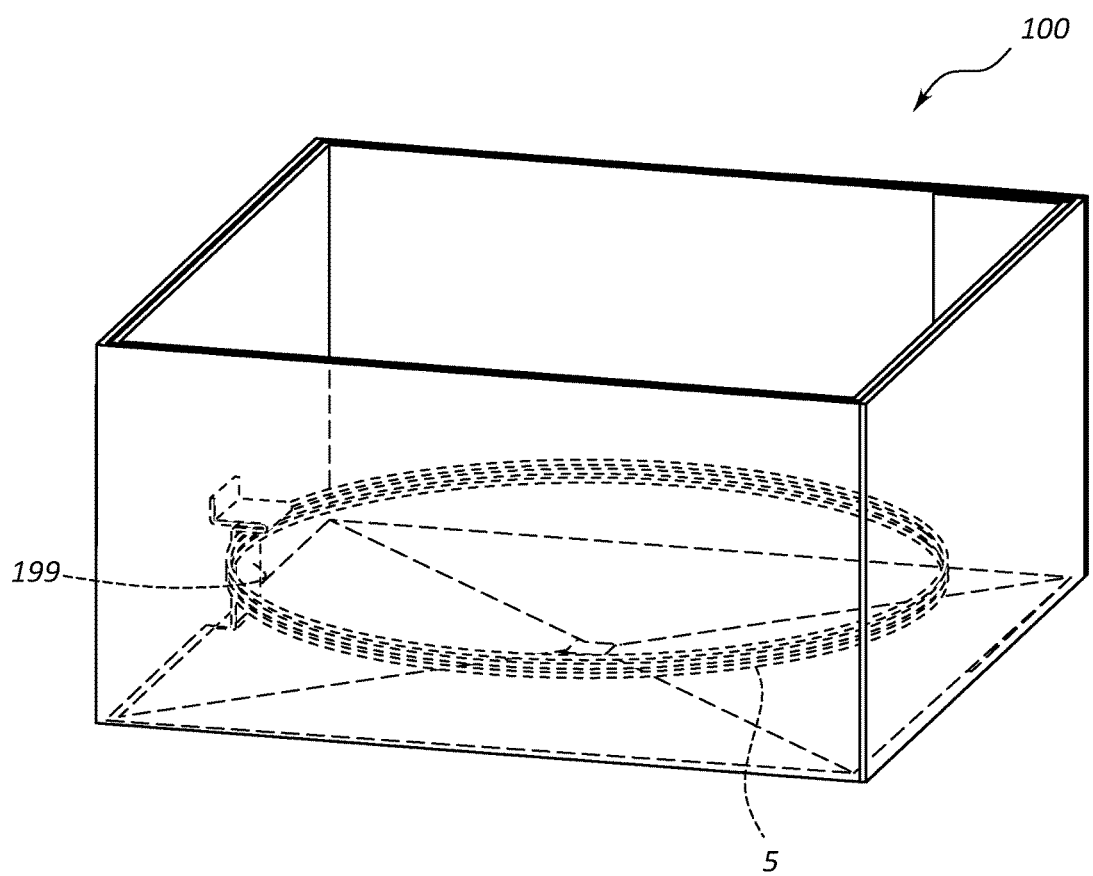
FIG. 16 is a perspective view of the collapsible container of FIGS. 7-15 with a folded protrusion extending inward from an interior wall the collapsible container.

In some embodiments, as shown in FIG. 16, the collapsible container 100 may further include a folded protrusion 199 that extends inward from an interior wall of the collapsible container 100 when the container is in an uncollapsed configuration. The folded protrusion 199 may be designed to contact one or more guidewires 5 disposed within the container, thereby serving as a ledge that can be used to retain a guidewire 5. While only one folded protrusion 199 is shown in FIG. 16, other embodiments may include multiple protrusions 199 that extend inward from the interior wall (e.g., one protrusion for each lateral side of the interior wall). In other embodiments (e.g., as shown in FIGS. 1-15), the collapsible container 100 may lack the folded protrusion 199.

Figure 17:
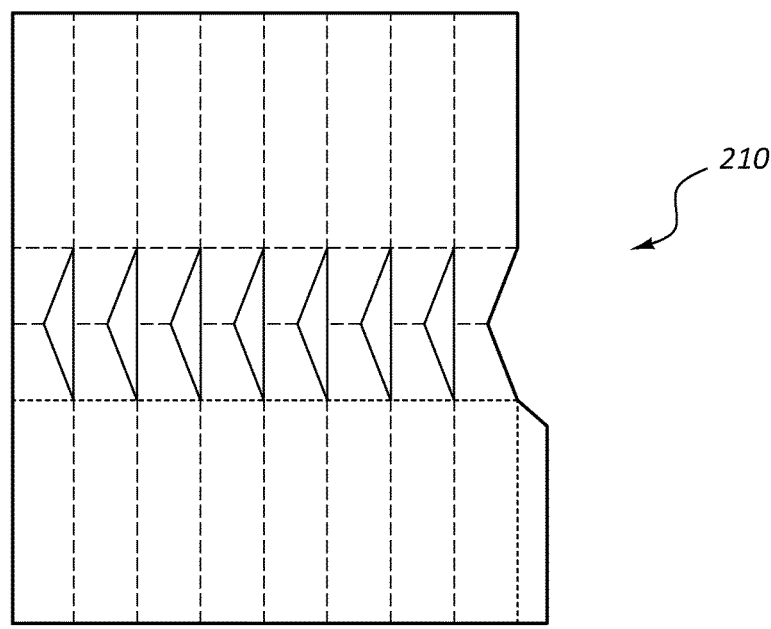
FIG. 17 is a top view of a first side of a foldable sheet, according to another embodiment.
Figure 18:
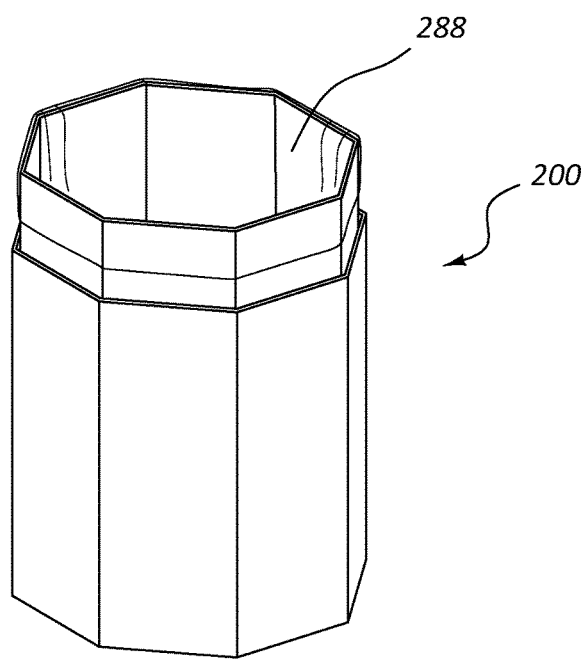
FIG. 18 is a perspective view of a collapsible container formed from the sheet of FIG. 17.
Figure 19:
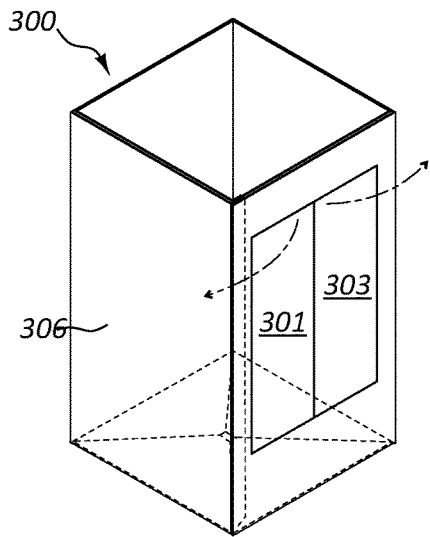
FIGS. 19, 20, 21, 22, and 23 provide perspective views of a collapsible container, according to another embodiment, in which the collapsible container includes a lid.

FIGS. 17 and 18 depict an embodiment of a sheet 210 and a collapsible container 200 that resemble the sheet 110 and the collapsible container 100 described above in certain respects. Accordingly, like features are designated with like reference numerals, with the leading digits incremented to "2." Relevant disclosure set forth above regarding similarly identified features thus may not be repeated hereafter. Moreover, specific features of the sheet 210, the collapsible container 200, and related components shown in FIGS. 1-16 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the sheet 210, the collapsible container 200 and related components depicted in FIGS. 17 and 18. Any suitable combination of the features, and variations of the same, described with respect to the sheet 110, the collapsible container 100, and related components illustrated in FIGS. 1-16 can be employed with the sheet 210, collapsible container, 200, and related components of FIGS. 17 and 18, and vice versa. This pattern of disclosure applies equally to further embodiments depicted in subsequent figures and described hereafter, wherein the leading digits may be further incremented.

The sheet 210 of FIG. 17 may be folded into the collapsible container 200 of FIG. 18 in a manner analogous to that described above in connection with the sheet 110 and the container 100 of FIGS. 1-16. The resulting collapsible container 200 is generally shaped as an octagonal prism. FIG. 18 shows an impermeable liner 288 that may be disposed within the container 200.

FIGS. 19-23 provide perspective views of a collapsible container 300 with a lid 50. The collapsible container 300 may be formed in a manner similar to that described above in connection with the collapsible container 100. As shown in FIGS. 19-23, the collapsible container 300 may include a plurality of flaps 301, 303 in an exterior wall 306 of the container 300. The plurality of flaps 301, 303 may be opened up to provide access to the lid 50 disposed therein. Stated differently, the lid 50 may initially be disposed between the exterior wall 306 and an interior wall of the container 300.

Figure 20:
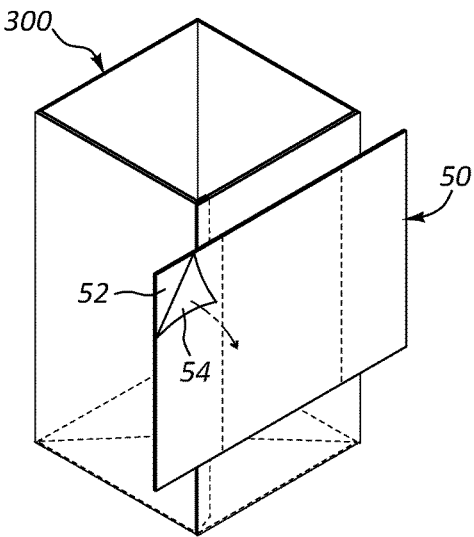

The lid 50 may then be removed from the opening formed by the flaps 301, 303. When removed from the opening formed by the flaps 301, 303, the lid 50 may initially include an adhesive sheet 52 and an adhesive cover 54. The adhesive cover 54 may then be removed as shown in FIG. 20 to expose the adhesive sheet 52.

Figure 21:
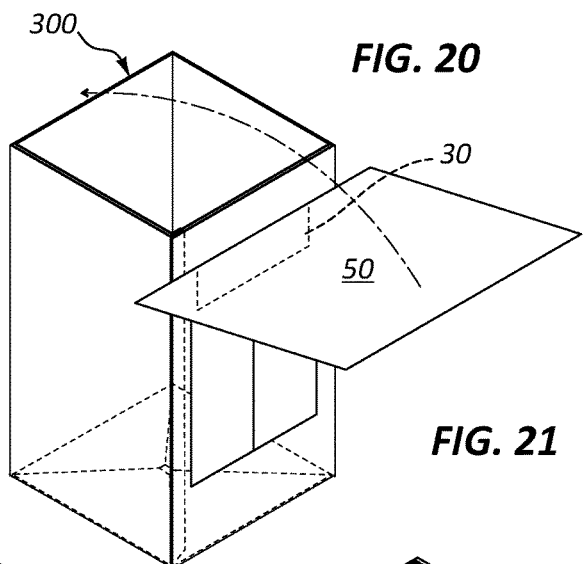
Figure 22:
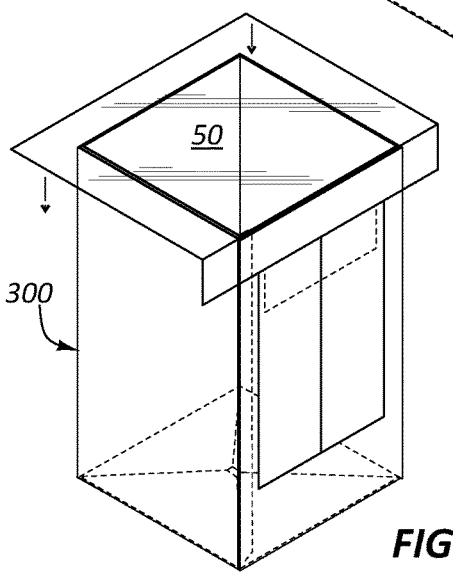
Figure 23:
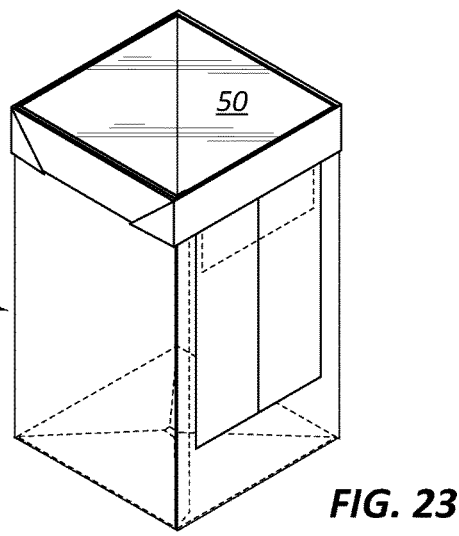

The lid 50 may then be rotated over the top of the container 300 as shown in FIG. 21. In some embodiments, one end of the lid 50 is attached to the container 300 via a fastener 30. Once disposed over the top of the container 300, portions of the lid 50 that extend beyond the perimeter of the top face of the container 300 may be folded as shown in FIGS. 22 and 23 to contact and adhere to the side walls of the container 300. In this manner, a lid may be placed over the top of the container 300 to at least partially seal the container 300.

In some embodiments, the lid 50 may be punctured, cut, torn, or otherwise compromised to add or remove material from the container 300. For example, in some embodiments a needle of a syringe may be inserted through the lid 50 to deliver medical waste into the collapsible container 300. In other or further embodiments, a straw may be inserted into the container 300 to facilitate removal of liquid within the container.

Figure 24:
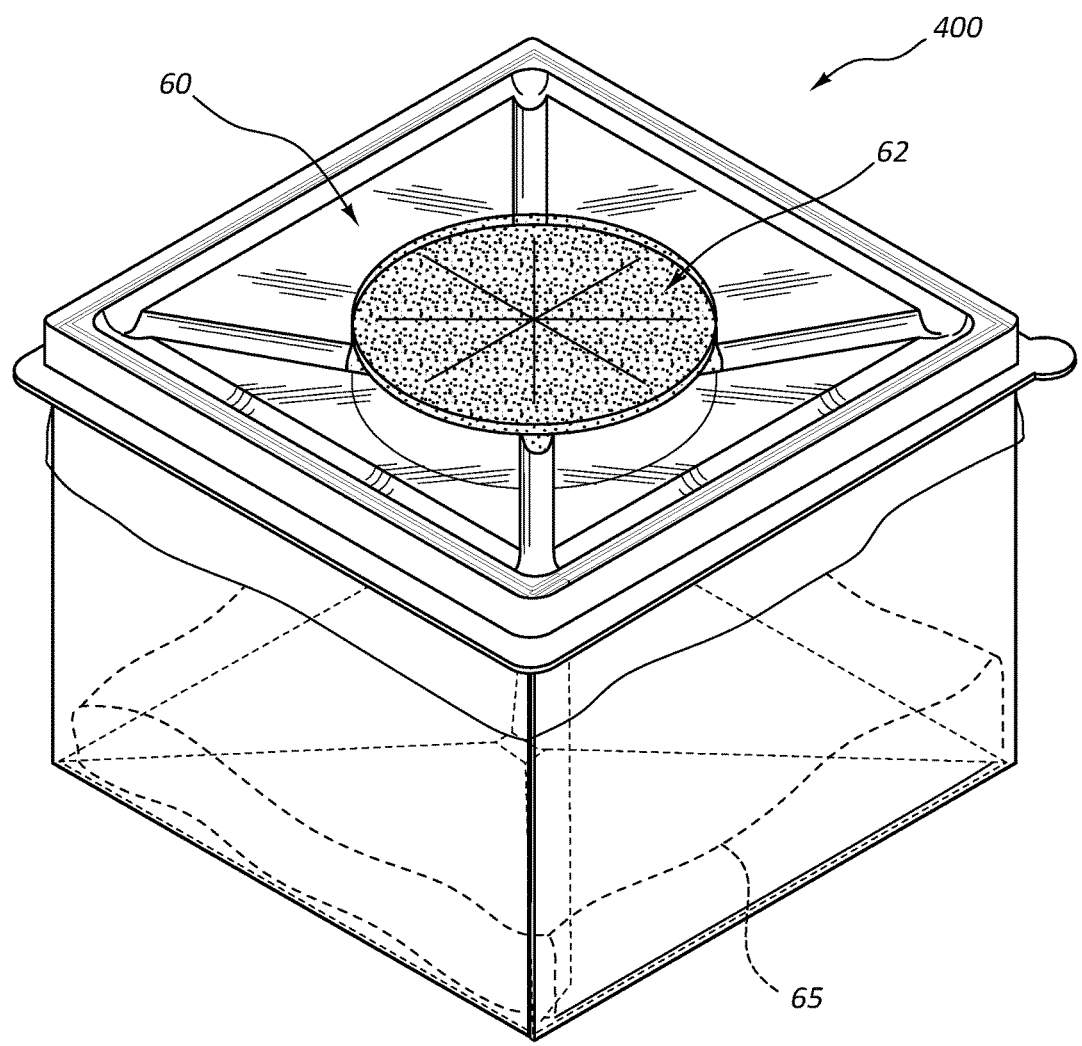
FIG. 24 is a perspective view of a collapsible container, according to another embodiment.

FIG. 24 is a perspective view of a collapsible container 400, according to another embodiment. The collapsible container 400 may include a removable lid 60. An absorbent pad 65 may be disposed within the container 400 to absorb liquid that is delivered to the container 400. The lid 60 may include a slit valve 62 that defines an input site. Liquid waste may be delivered through the slit valve 62 and into the absorbent pad 65. For example, a distal end of a syringe filled with fluid from a patient may be inserted across the slit valve 62 to deliver fluid to the absorbent pad 65 within the collapsible container 400. The slit valve 62 and the lid 60 may together function as a splash guard that prevents splashing or spilling of materials delivered into the container 400. In some embodiments, the slit valve 62 is made of foam.

Figure 25:
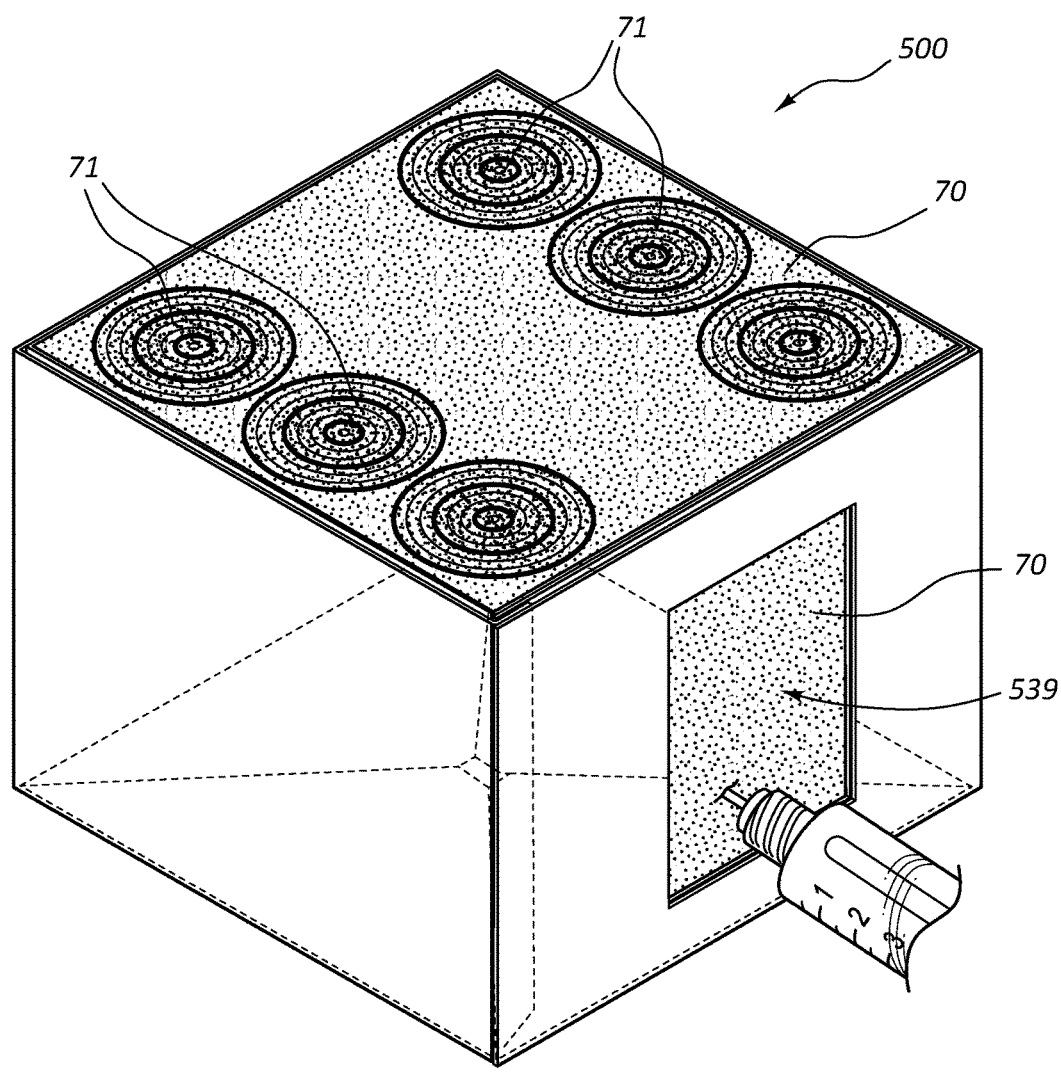
FIG. 25 is a perspective view of a collapsible container, according to another embodiment.

FIG. 25 is a perspective view of a collapsible container 500, according to another embodiment. The collapsible container 500 is generally analogous to the collapsible container 100. However, the collapsible container 500 further includes a window 539 that provides access to a cushion 70 disposed within the container 500. The cushion 70 may be configured to receive and secure one or more sharp members (e.g., sharp medical instruments such as a needle, a scalpel, etc.). For example, during some medical procedures, a practitioner may insert a sharp medical instrument through the opening at the top of the container 500 or through the window 539 to insert the instrument into the cushion 70. In this manner, the assembly including both the container 500 and the cushion 70 may function as a temporary instrument holder.

In some embodiments, the cushion 70 is a relatively uncompressible closed-cell foam (e.g., styrofoam). In such embodiments, the cushion 70 may be inserted into the collapsible container 500 by the practitioner after the collapsible container 500 is formed in the uncollapsed configuration. In other embodiments, the cushion 70 is a relatively compressible open-cell foam. In some embodiments using a relatively compressible cushion 70, the cushion 70 may be disposed and compressed within the container 500 when the container 500 is in the collapsed state. Such compression may be maintained using a vacuum seal or via mechanical means. Subsequently, as the container 500 is transitioned to the uncollapsed configuration, the cushion 70 may spring into its uncompressed state. In some embodiments, the force provided by the cushion 70 as it is uncompressed causes the transition of the container 500 from the collapsed configuration to the uncollapsed configuration. In some embodiments, the cushion 70 may include indicia 71 (e.g., one or more targets) that suggest locations for insertion of one or more sharp members.

Figure 26:
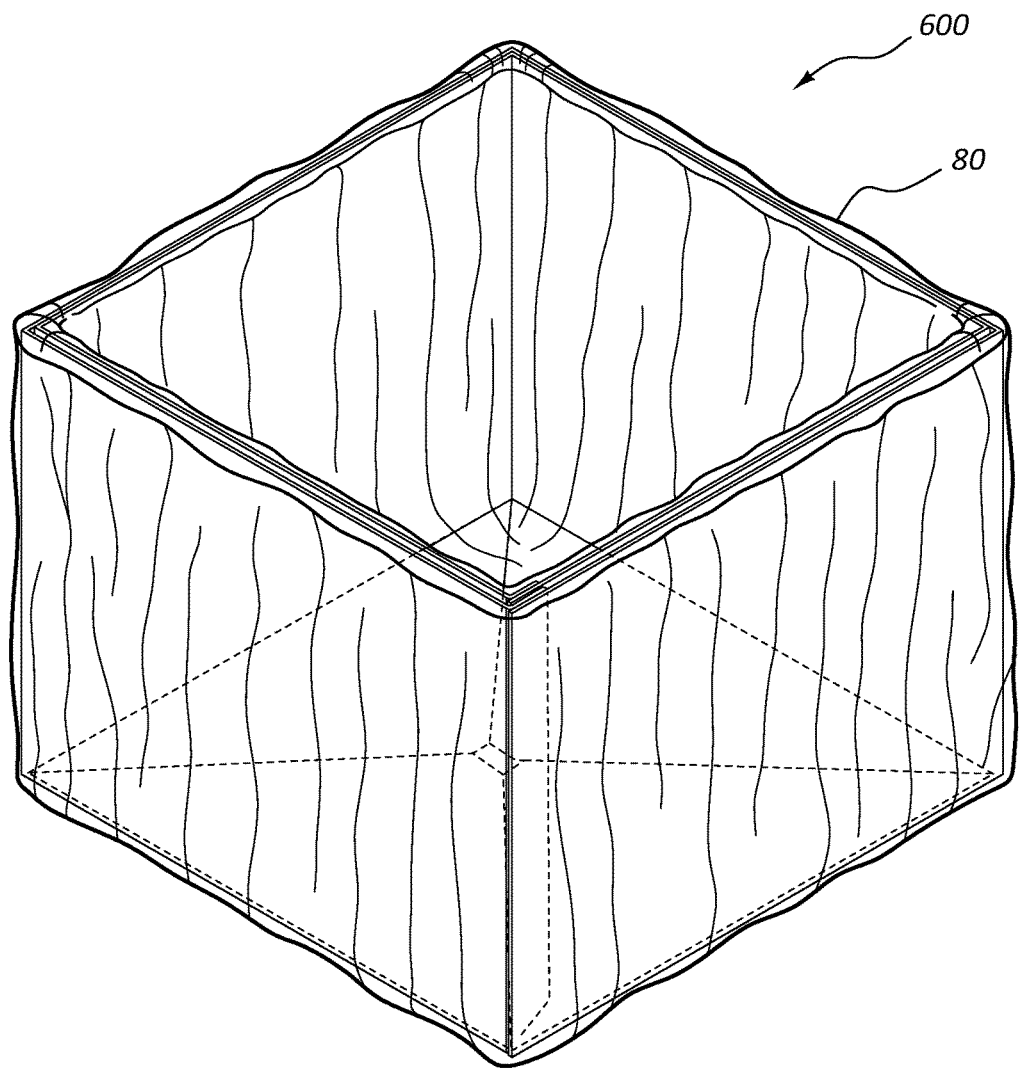
FIG. 26 is a perspective view of a collapsible container, according to another embodiment.

FIG. 26 provides a perspective view of a collapsible container 600 and a bag 80. In the depicted embodiment, the bag 80 completely surrounds the container 600, although the bag 80 need not surround the container 600 in all embodiments.

In some embodiments, the collapsible container 600 can transition between the collapsed and uncollapsed configuration while inside of the bag 80. For example, the collapsible container 600 may be initially shipped and stored in the collapsed configuration within the bag 80 and then, while still in the bag 80, transition to an uncollapsed configuration.

In some embodiments, the bag is designed to snugly fit around the container 600. In other embodiments, the bag loosely fits around the container to provide excess material to tie off the bag for disposal. In other or further embodiments, the bag includes a drawstring, a ziplock fastener, tape, etc., for tying off the bag for disposal. In some embodiments, the bag is analogous to the bag 288 depicted in FIG. 18.

Figure 27:
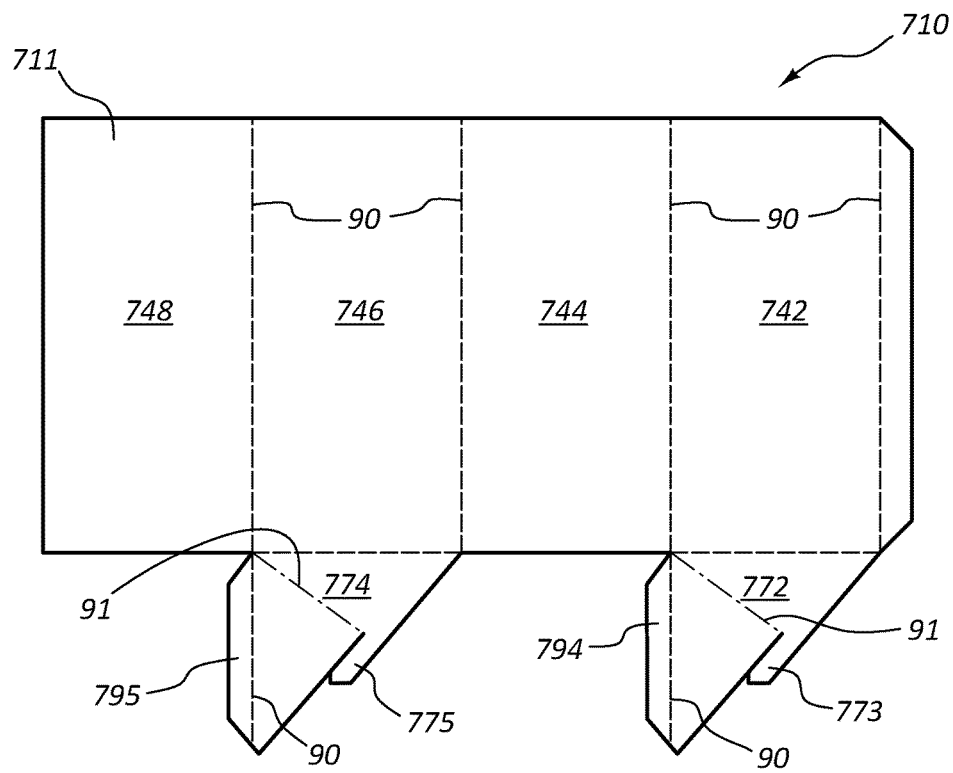
FIG. 27 is a top view of a foldable sheet, according to another embodiment.
Figure 28:
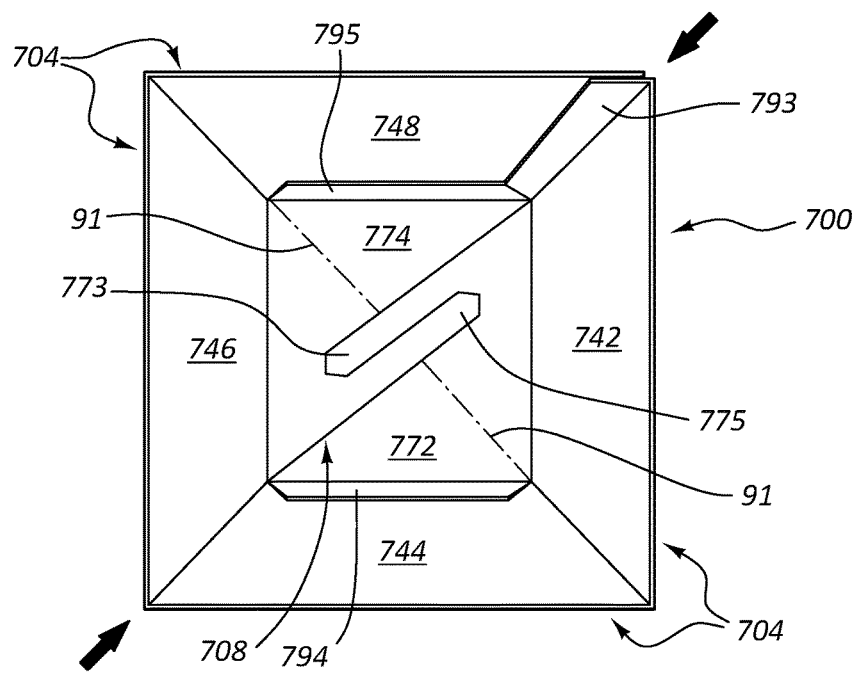
FIG. 28 is a top view of a collapsible container formed from the sheet of FIG. 27.

FIG. 27 is a top view of a first side 711 of a foldable sheet 710 for forming the collapsible, auto-bottom container 700 depicted in FIG. 28. The foldable sheet 710 includes a plurality of folds 90, 91. The dashed lines having dashes of equal length for each of the folds 90 indicate that the planar panels on either side of the fold tend to go into the page relative to the fold. The dashed lines of unequal length for each of the folds 91 indicate that the planar panels on either side of the fold tend to come out of the page relative to the fold.

The sheet 710 may be folded such that each of the wall segments 742, 744, 746, 748 form a side wall 704 for the container 700. The base segments 772, 774 cooperate to form a base 708 of the container 700. For example, in the depicted embodiment, a hook 773 of the first base segment 772 and a hook 775 of the second base segment 774 engage with one another to facilitate formation a stable base 708.

The tabs 793, 794, 795 may facilitate coupling of planar segments to one another. For example, the first tab 793 may be configured to couple the first planar wall segment 742 to the fourth planar wall segment 748. The second tab 794 may be configured to couple the first base segment 772 to the second wall segment 744 (e.g., via an adhesive). The third tab 795 may be configured to couple to the second base segment 774 to the fourth wall segment 748.

The container 700 of FIG. 28 may collapse into a substantially planar configuration by pushing the folds 91 upward (i.e., out of the page) while pushing opposite edges of the box toward one another as shown by the arrows. Manipulation of the container 700 in this manner disengages the hook 773 from the hook 775, thereby allowing for collapse of the container 700.

Figure 29:
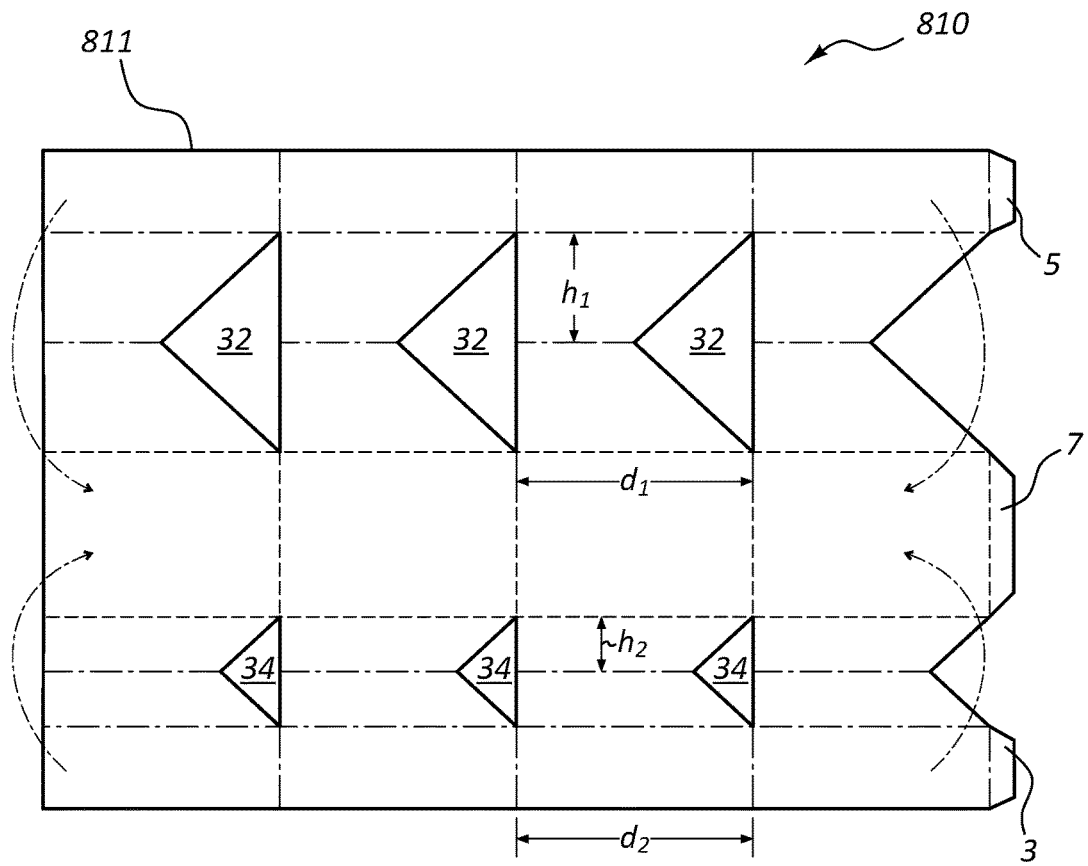
FIG. 29 is a view of a foldable sheet, according to another embodiment.
Figure 30:
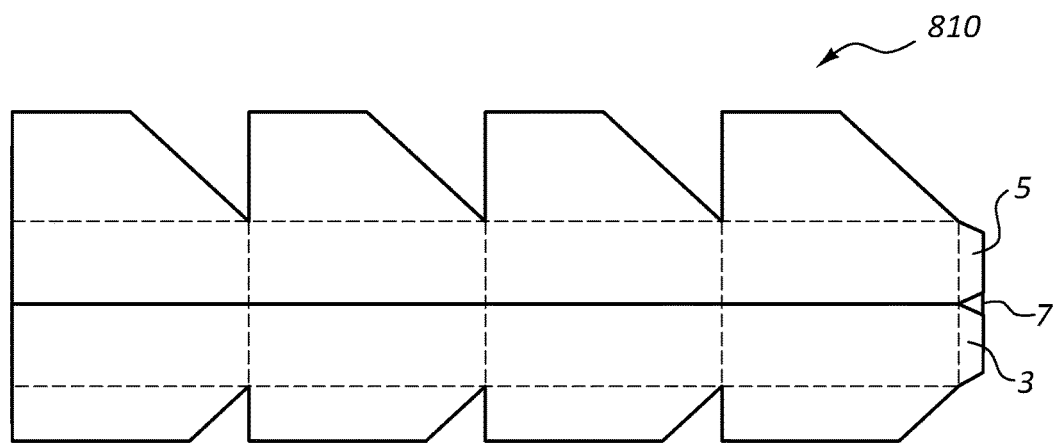
FIGS. 30 and 31 are views of the foldable sheet of FIG. 29 in differently folded states.
Figure 31:
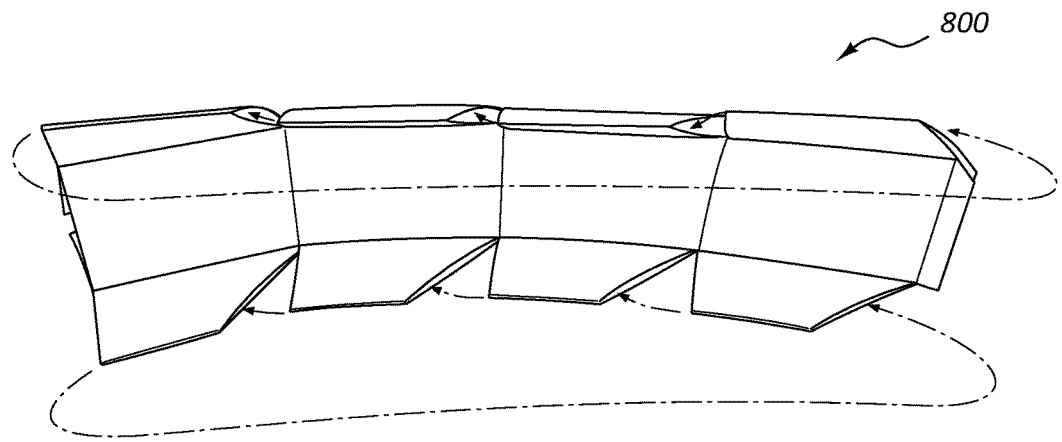
Figure 32:
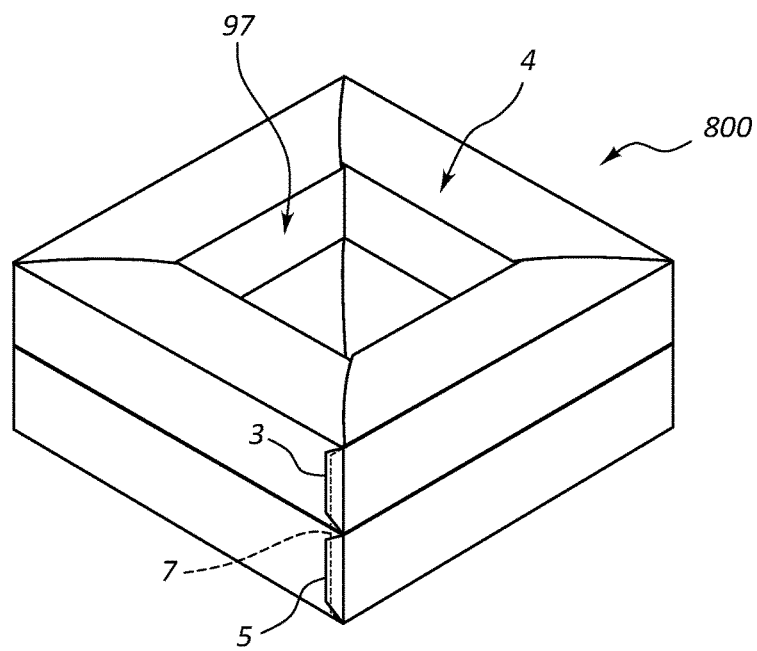
FIG. 32 is a perspective view of a collapsible container formed from the sheet of FIGS. 29-31, with the collapsible container in an uncollapsed configuration.

FIG. 29 provides a top view of a first side 811 of a foldable sheet 810 for making the collapsible container 800 of FIGS. 30, 31, and 32. The foldable sheet 810 includes a plurality of folds analogous to those depicted for the container 100. A fold denoted by a dashed line having dashes of unequal length indicates that the planar panels on either side of the fold tend to come out of the page relative to the fold, while a fold denoted by a dashed line having dashes of equal length indicates that the planar panels on either side of the fold tend to go into the page relative to the fold.

In the depicted embodiment, the foldable sheet 810 includes a first set of openings 32 and a second set of openings 34, wherein the openings 34 are smaller than the openings 32. The total number of openings 32, 34 may be two less than twice the number of lateral sides of the container 800 formed from the foldable sheet 810. The ratio of the distance $h_1/d_1$ as shown in FIG. 29 is approximately 0.5. This relationship between $h_1$ and $d_1$ allows for the formation of a closed base (i.e., a base with substantially no aperture). In contrast, the ratio of the distance $h_2/d_2$ as shown in FIG. 29 is less than 0.5. This relationship between $h_2$ and $d_2$ allows for the formation of a lid 4 having an aperture 97 (see FIG. 32). One of ordinary skill in the art, with the benefit of this disclosure, will recognize that the size of the aperture 97 of the lid 4 may be controlled by adjusting the height of the openings. A skilled artisan, with the benefit of this disclosure will also recognize that, in embodiments where the base of the container is rectangular in shape, the ratio of $h_1/d_1$ may be approximately 0.5 for the "short" side of the rectangular container, but not for the "long" side of the rectangular container.

From the unfolded state shown in FIG. 29, the sheet 810 may be folded into a collapsible box 800 in a manner analogous to that described above in connection with the container 100. More particularly, the edges of the sheet 810 may be folded inward as indicated by the arrows of FIG. 29 such that the sheet 810 is folded as shown in FIG. 30. Then, the sheet 810 may be turned over and rotated to the position shown in FIG. 31. From the position shown in FIG. 31, corners of the base segments and corners of the lid segments may be inserted into corresponding slots as indicated by the arrows shown in FIG. 31. The collapsible container 800 shown in FIG. 32 may then be formed by both coupling the exterior tabs 3, 5 to an exterior wall of the container 800 and coupling the interior tab 7 to an interior wall of the container 800.

Figure 33:
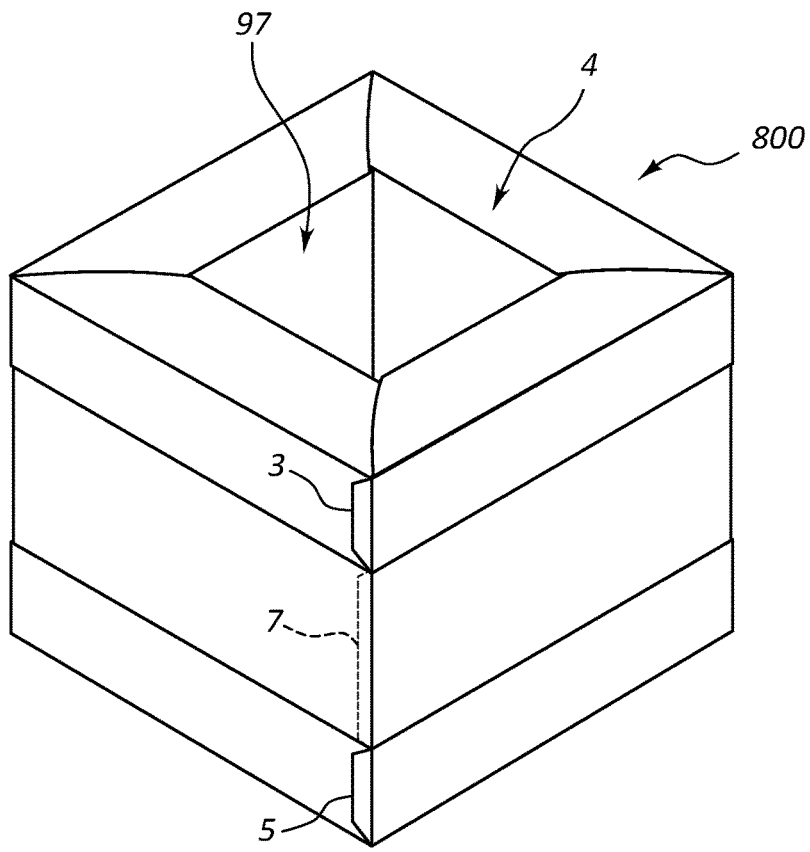
FIG. 33 is a perspective view of the collapsible container of FIG. 32 in an extended configuration.
Figure 34:
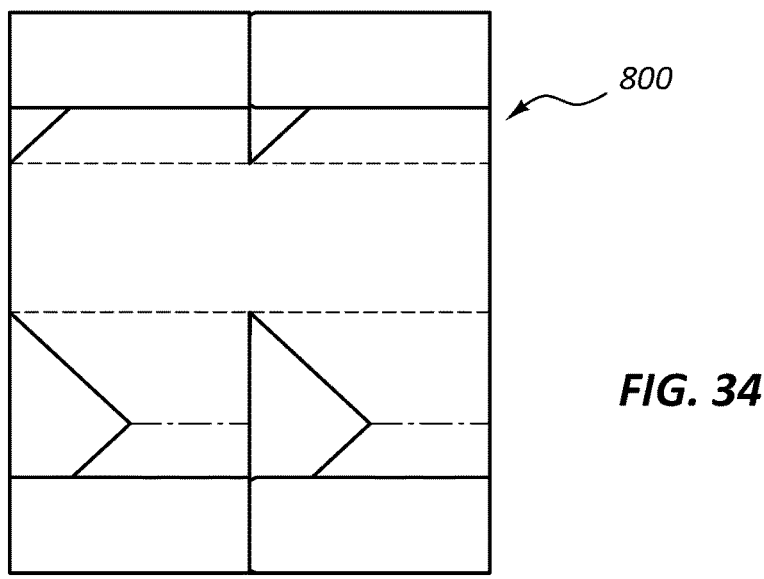
FIG. 34 is a perspective view of the collapsible container of FIGS. 32 and 33 in a collapsed configuration.

The collapsible container 800 may transition from the uncollapsed configuration shown in FIG. 32 to the collapsed configuration (FIG. 34) in a manner analogous to that described above in connection with the collapsible container 100. For example, the collapsible container 800 may transition from the uncollapsed configuration to the collapsed configuration (and vice versa) via an extended configuration (shown in FIG. 33).

In some embodiments, a slit valve (not shown) may be associated with the lid 4 of the container 800. In other words, the slit valve may be coupled to the lid in some embodiments to at least partially cover the aperture 97. In embodiments that include a slit valve, the slit valve and the lid 4 may together function as a splash guard that prevents splashing or spilling of materials delivered into the container 800.

Figure 35:
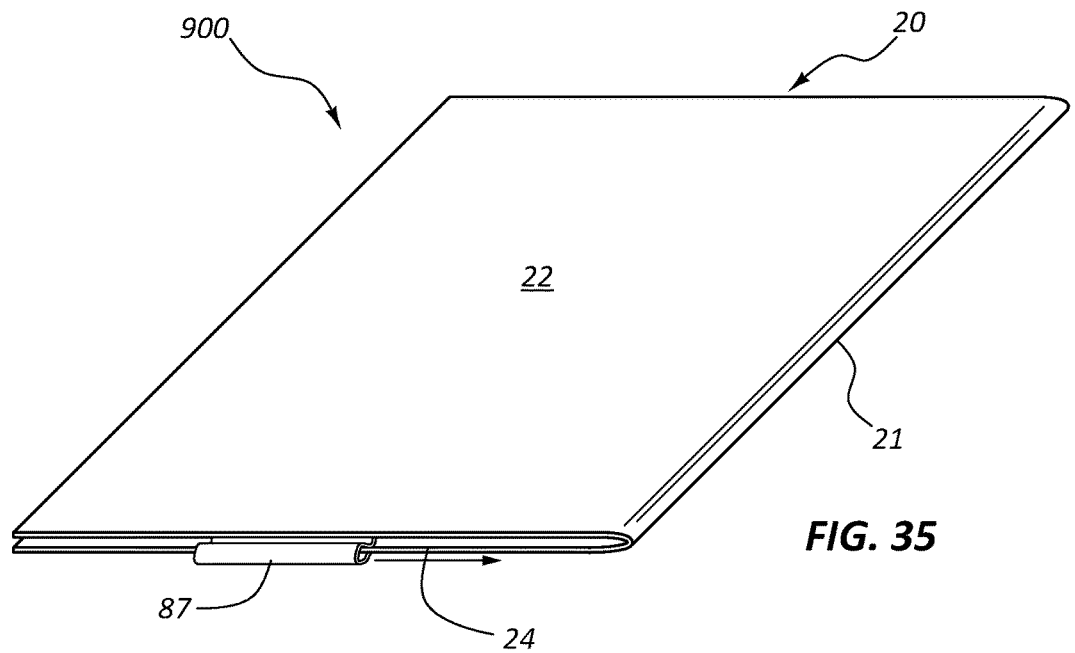
FIG. 35 is a perspective view of a container according to another embodiment, in a compact storage configuration.
Figure 36:
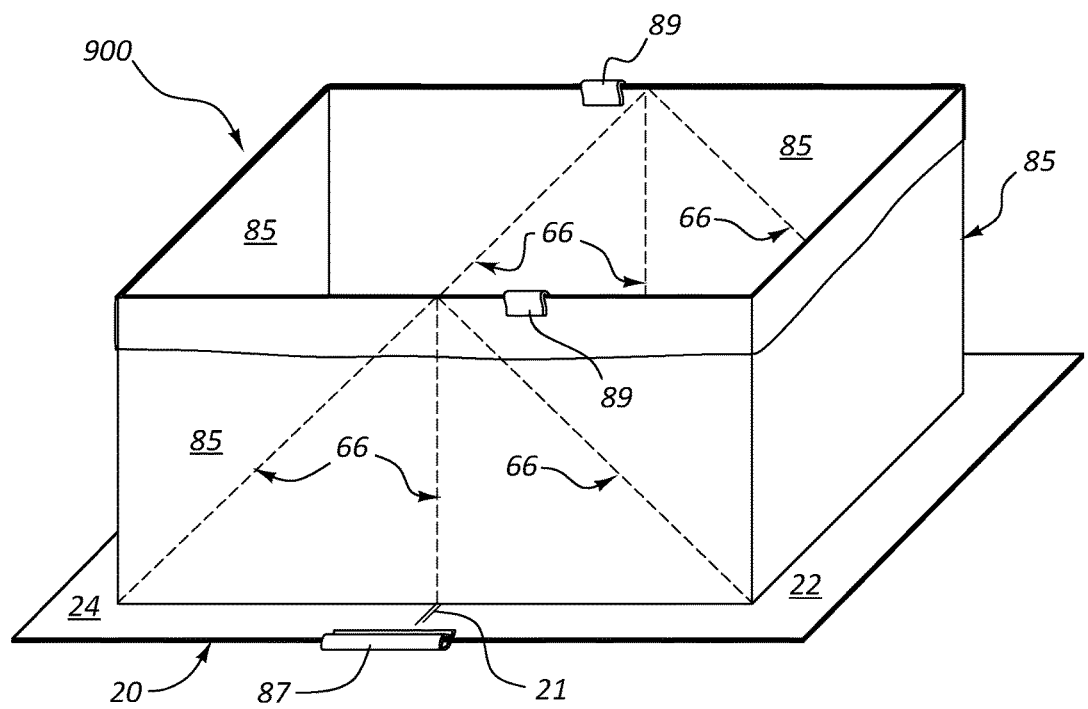
FIG. 36 is a perspective view of the container of FIG. 35 in a configuration for use.

FIGS. 35 and 36 provide perspective views of a container 900 according to another embodiment. More specifically, FIG. 35 provides a perspective view of the container 900 in a compact storage state, while FIG. 36 provides a perspective view of the container 900 in a configuration for use.

The container 900 includes a board 20 that is designed to fold across a crease 21. In the compact storage configuration, the board 20 is folded such that the a first portion 22 of the board is disposed on top of a second portion 24 of the board 20. To transition the container 900 from the compact storage configuration shown in FIG. 35 to the configuration for use shown in FIG. 36, the first portion 22 of the board 20 may be rotated about the crease 21 such that the board 20 is disposed in the open configuration as shown in FIG. 36. As the first portion 22 of the board 20 is rotated in this manner, the walls 85 of the container may pop up from the board 20 in a manner analogous to the emergence of a three-dimensional structure from a pop-up book.

One or more of the walls 85 of the container 900 may include a plurality of folds 66 that are designed to allow the walls 85 to lay flat when the board 20 is folded on top of itself, while allowing the walls 85 to extend substantially perpendicular to the board 20 when the board 20 is disposed in an open configuration.

In some embodiments, when the container 900 is in the open configuration, one or more clamps 87 may be attached or otherwise coupled to the board 20 to hold the board 20 in the open configuration. For example, in some embodiments, once the board 20 has been opened, a clamp 87 may be slid along the periphery of the board 20 to prevent the board 20 from reverting back to the compact storage configuration (e.g., the configuration shown in FIG. 35). In some embodiments, one or more clamps 89 may be attached or otherwise coupled to the walls 85 to help maintain the container 900 in the open configuration.

In some embodiments, containers, such as those described above, may be combined to form a more complex container. For example, two containers may be coupled (e.g., attached) to one another to form a container with two distinct receptacles. In some embodiments, the receptacles are disposed adjacent to one another (e.g., in a side-by-side arrangement). In some embodiments, a first container is disposed within and coupled to a second container.

As noted above, the containers described above may be used for any suitable purpose. For example, in some embodiments, the containers may be used as trash receptacles. More specifically, the containers may be used to receive medical waste, such as solid or liquid extracted from a patient (e.g., via a syringe). In some embodiments, the contents of a medical device, such as a syringe, may be delivered into the container. In some embodiments, an absorbent material, such as an absorbent pad, may be placed inside of the container to soak up liquid delivered into the container. In some embodiments, the container includes a lid and/or a slit valve that prevents splashing of liquid outside of the container when liquid is delivered into the container. In some embodiments, the containers are designed to hydrate one or more guidewires or other medical instruments. In some embodiments, a cushion or other material may be inserted into the container to hold sharp medical instruments.

Any methods disclosed a herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A collapsible container comprising:
   an interior side wall comprising a plurality of planar wall segments;
   an exterior side wall comprising a plurality of planar wall segments;
   wherein the collapsible container is configured to transition from a collapsed configuration in which the planar wall segments of the interior side wall and the planar wall segments of the exterior side wall lie substantially in a single plane to an uncollapsed configuration in which the interior side wall and the exterior side wall each form a convex polygon with internal angles that are each greater than or substantially equal to 30°;
   a slit in a planar wall segment of the interior side wall configured to provide an inward protruding tab defining a horizontally disposed surface,
   wherein the planar wall segment comprising the slit forms a corner of the convex polygon with each interior planar wall segment disposed adjacent the planar wall segment comprising the slit.

2. The collapsible container of claim 1, wherein all internal angles of the convex polygon are greater than or substantially equal to 90°.

3. The collapsible container of claim 2, wherein the convex polygon is a regular polygon and wherein the transition from the collapsed configuration to the uncollapsed configuration further comprises displacing the interior side wall in a downward direction such that the interior side wall is disposed directly inside of the exterior side wall.

4. The collapsible container of claim 3, wherein the regular polygon is selected from the group consisting of a square, a regular hexagon, and a regular octagon.

5. The collapsible container of claim 1, wherein the interior wall and the exterior wall are portions of a single foldable sheet.

6. The collapsible container of claim 5, wherein the single foldable sheet comprises cellulose.

7. The collapsible container of claim 6, wherein the single foldable sheet, when in an unfolded configuration forms a single layer, and defines a plurality of openings.

8. The collapsible container of claim 7, wherein each opening of the plurality of openings comprises a tapered end and a non-tapered end disposed opposite the tapered end; and
wherein each opening of the plurality of openings is oriented such that the tapered ends of the opening all point in the same direction when the single foldable sheet is in an unfolded configuration to form a single layer.

9. The collapsible container of claim 8, wherein each opening of the plurality of openings is triangular in shape when the single foldable sheet is in an unfolded configuration to form a single layer.

10. The collapsible container of claim 9, wherein the number of openings of the single foldable sheet is one less than both the number of planar wall segments of the interior wall and the number of planar wall segments of the exterior wall.

11. The collapsible container of claim 10, further comprising a liquid-impermeable liner.

12. The collapsible container of claim 10, further comprising a lock that, when engaged, prevents transitioning of the collapsible container from the uncollapsed configuration to the collapsed configuration.

13. The collapsible container of claim 1, wherein the uncollapsed configuration comprises an open top end and a closed base.

14. The collapsible container of claim 1, wherein the external wall comprises no slit.

15. A collapsible container configured to transition from a collapsed configuration to an uncollapsed configuration, the collapsible container comprising:
a sheet of foldable material, the sheet comprising a plurality of openings that lie along a longitudinal axis of the sheet when the sheet is disposed flat as a single layer;
wherein the collapsible container is configured to transition from a collapsed configuration in which the collapsible container is disposed in substantially a single plane to an uncollapsed configuration in which the collapsible container forms a three-dimensional structure having a plurality of lateral sides and a base;
wherein the number of openings that lie along the longitudinal axis of the sheet is one less than the number of lateral sides of the three-dimensional structure;
wherein the plurality of lateral sides and the base are portions of the sheet of foldable material;
wherein an interior side wall and an exterior side wall form the plurality of lateral sides of the three-dimensional structure;
wherein the interior side wall comprises a slit defining a first deflectable tab and the exterior side wall comprises a slit defining a second deflectable tab such that the first deflectable tab is aligned with the second deflectable tab when the collapsible container is in the uncollapsed configuration;
wherein the first deflectable tab and the second deflectable tab are each formed of a single fold; and
wherein the first deflectable tab or the second deflectable tab defines a plane extending uninterrupted across an entire interior of the three-dimensional structure.

16. The collapsible container of claim 15, wherein the collapsible container is configured to transition from the collapsed configuration to the uncollapsed configuration by displacing the interior wall and the exterior wall such that both the interior wall and the exterior wall form the three-dimensional structure and subsequently displacing the interior side wall in a downward direction such that the interior wall is disposed directly inside of the exterior wall.

17. The collapsible container of claim 15, wherein:
the interior wall comprises a plurality of planar wall segments;
the exterior wall comprises a plurality of planar wall segments; and
the sheet comprises a first tab for coupling a first planar wall segment of the exterior wall to a second planar wall segment of the exterior wall.

18. The collapsible container of claim 17, wherein the sheet further comprises a second tab for coupling a first planar wall segment of the interior wall to a second planar wall segment of the interior wall.

19. The collapsible container of claim 18, wherein each opening of the plurality of openings comprises a tapered end and a non-tapered end disposed opposite the tapered end; and
wherein the plurality of openings are oriented such that tapered ends of the openings all point in the same direction.

20. The collapsible container of claim 19, wherein each opening of the plurality of openings is shaped as an isosceles triangle.

21. The collapsible container of claim 20, wherein the foldable sheet further comprises a notch that lies along the longitudinal axis of the foldable sheet; and wherein the notch comprises a tapered end.

22. A method of manipulating a collapsible container, the method comprising:
obtaining a collapsible container in a substantially planar configuration, the collapsible container comprising:
an interior wall comprising a plurality of planar wall segments; and
an exterior wall comprising a plurality of planar wall segments;
manipulating the collapsible container to adopt a three-dimensional structure in which the planar wall segments of the interior wall and the planar wall segments of the exterior wall each form a convex polygon; and
displacing the interior wall in a downward direction such that the interior wall is disposed directly inward of the exterior wall, wherein displacing the interior wall in a downward direction causes formation of a base of the collapsible container; and
deflecting a tab defined by a single slit in one of the interior and exterior walls at least partially through an opening defined by a single slit in the other one of the interior and exterior walls,
wherein the tab is centrally located in the one of the interior and exterior walls between adjacent interior walls or between adjacent exterior walls, respectively.

23. The method of claim 22, wherein the convex polygon is a regular polygon.

24. The method of claim 22, further comprising collapsing the collapsible container to the substantially planar configuration after manipulating the collapsible container to adopt the three-dimensional structure.

25. A method of manufacturing a container, the method comprising:
- obtaining a foldable sheet comprising a plurality of openings that lie along a longitudinal axis of the sheet;
- folding the foldable sheet to form a three-dimensional structure comprising a plurality of lateral side walls and a base; and
- coupling a first lateral side wall of the plurality of lateral side walls to a second lateral side wall of the plurality of lateral side walls;
- wherein the container is a collapsible container, and
- forming a slit in a lateral side wall configured to provide a protrusion on an inner surface of the lateral side wall,
- wherein the entirety of the slit is formed in the lateral side wall, and
- wherein the slit is centrally located between adjacent lateral side walls.

\* \* \* \* \*